US011826321B2

(12) United States Patent
Harris et al.

(10) Patent No.: US 11,826,321 B2
(45) Date of Patent: Nov. 28, 2023

(54) CYCLOBENZAPRINE TREATMENT FOR AGITATION, PSYCHOSIS AND COGNITIVE DECLINE IN DEMENTIA AND NEURODEGENERATIVE CONDITIONS

(71) Applicant: TONIX PHARMA HOLDINGS LIMITED, Dublin (IE)

(72) Inventors: Herbert W. Harris, Chapel Hill, NC (US); Seth Lederman, South Dartmouth, MA (US)

(73) Assignee: Tonix Pharma Holdings Limited, Dublin (IE)

( * ) Notice: Subject to any disclaimer, the term of this patent is extended or adjusted under 35 U.S.C. 154(b) by 0 days.

(21) Appl. No.: 16/215,952

(22) Filed: Dec. 11, 2018

(65) Prior Publication Data
US 2019/0175525 A1    Jun. 13, 2019

Related U.S. Application Data

(60) Provisional application No. 62/597,284, filed on Dec. 11, 2017.

(51) Int. Cl.
| A61K 31/135 | (2006.01) |
| A61K 45/06  | (2006.01) |
| A61P 25/28  | (2006.01) |
| A61K 9/20   | (2006.01) |
| A61K 9/00   | (2006.01) |
| A61K 9/14   | (2006.01) |

(52) U.S. Cl.
CPC ............ A61K 31/135 (2013.01); A61K 9/006 (2013.01); A61K 9/0056 (2013.01); A61K 9/2018 (2013.01); A61K 9/2059 (2013.01); A61K 45/06 (2013.01); A61P 25/28 (2018.01); A61K 9/145 (2013.01)

(58) Field of Classification Search
CPC .............................. A61K 31/135; A61P 25/28
See application file for complete search history.

(56) References Cited

U.S. PATENT DOCUMENTS

| 3,882,246 A * | 5/1975 | Share .................. A61K 31/135 |
| | | 514/654 |
| 4,788,063 A | 11/1988 | Fisher |
| 4,968,507 A | 11/1990 | Zentner |
| 5,073,543 A | 12/1991 | Marshall |
| 5,120,548 A | 6/1992 | McClelland |
| 5,439,686 A | 8/1995 | Desai |
| 5,498,421 A | 3/1996 | Grinstaff |
| 5,591,731 A | 1/1997 | Kennedy |
| 5,591,767 A | 1/1997 | Mohr |
| 5,639,476 A | 6/1997 | Oshlack |
| 5,674,533 A | 10/1997 | Santus |
| 5,733,566 A | 3/1998 | Lewis |
| 6,096,331 A | 8/2000 | Desai |
| 6,248,363 B1 | 6/2001 | Patel |
| 6,267,985 B1 | 7/2001 | Chen |
| 6,309,663 B1 | 10/2001 | Patel |
| 6,358,944 B1 | 3/2002 | Lederman |
| 6,383,471 B1 | 5/2002 | Chen |
| 6,395,788 B1 | 5/2002 | Iglehart |
| 6,506,405 B1 | 1/2003 | Desai |
| 6,537,579 B1 | 3/2003 | Desai |
| 6,541,523 B2 | 4/2003 | Iglehart |
| 6,649,186 B1 | 11/2003 | Robinson |
| 6,720,001 B2 | 4/2004 | Chen |
| 6,749,868 B1 | 6/2004 | Desai |
| 6,753,006 B1 | 6/2004 | Desai |
| 6,761,903 B2 | 7/2004 | Chen |
| 7,105,486 B2 | 9/2006 | Mickle |
| 7,223,735 B2 | 5/2007 | Mickle |
| 7,532,935 B2 | 5/2009 | Maschino |
| 7,655,630 B2 | 2/2010 | Mickle |
| 7,658,945 B2 | 2/2010 | Singh |
| 7,659,253 B2 | 2/2010 | Mickle |
| 7,659,254 B2 | 2/2010 | Mickle |
| 7,662,787 B2 | 2/2010 | Mickle |
| 7,662,788 B2 | 2/2010 | Mickle |
| 7,671,030 B2 | 3/2010 | Mickle |
| 7,671,031 B2 | 3/2010 | Mickle |
| 7,674,774 B2 | 3/2010 | Mickle |
| 7,678,770 B2 | 3/2010 | Mickle |
| 7,678,771 B2 | 3/2010 | Mickle |
| 7,682,628 B2 | 3/2010 | Singh |
| 7,687,466 B2 | 3/2010 | Mickle |
| 7,687,467 B2 | 3/2010 | Mickle |

(Continued)

FOREIGN PATENT DOCUMENTS

| EP | 2233134 | 9/2010 |
| FR | 2635461 | 2/1990 |

(Continued)

OTHER PUBLICATIONS

Sura et al., Prevalence and Determinants of Anticholinergic Medication Use in Elderly Dementia Patients, Drugs Aging (2013) 30: 837-844.*
Verma et al., Contribution of PTSD/POW history to behavioral disturbances in dementia, International Journal of Geriatric Psychiatry, 2001; 16-356-360.*
Amital et al., "Posttraumatic stress disorder, tenderness, and fibromyalgia syndrome: are they different entities?," Journal of Psychosomatic Research, 61(5):663-669 (2006).
Anxiety Disorders, Diagnostic and Statistical Manual of Mental Disorders, 4th Edition DSM-IV, American Psychiatric Association, pp. 393-444 (1994).
Arnold et al., "Antidepressant treatment of fibromyalgia. A metaanalysis and review," Psychosomatics, 41:104-113 (2000).
Assal et al., "Association of the serotonin transporter and receptor gene polymorphisms in neuropsychiatric symptoms in Alzheimer disease," Archives of Neurology, 61(8):1249-53 (2004).

(Continued)

Primary Examiner — Svetlana M Ivanova
(74) Attorney, Agent, or Firm — HALEY GUILIANO LLP; James F. Haley, Jr.; Stacey W. Chung

(57) ABSTRACT

Compositions comprising cyclobenzaprine, and methods for the treatment or prevention of agitation, psychosis and/or cognitive decline and associated symptoms thereof in dementia and other neurodegenerative conditions.

7 Claims, No Drawings

(56) References Cited

U.S. PATENT DOCUMENTS

| | | | |
|---|---|---|---|
| 7,700,561 B2 | 4/2010 | Mickle | |
| 7,713,936 B2 | 5/2010 | Mickle | |
| 7,718,619 B2 | 5/2010 | Mickle | |
| 7,723,305 B2 | 5/2010 | Mickle | |
| RE41,884 E | 10/2010 | Garavilla | |
| 7,820,788 B2 | 10/2010 | Desai | |
| 7,923,536 B2 | 4/2011 | Desai | |
| 8,093,300 B2 | 1/2012 | Lederman | |
| 8,137,734 B2 | 3/2012 | Venkatesh | |
| 8,138,229 B2 | 3/2012 | Desai | |
| 8,216,610 B2 | 7/2012 | Roberts | |
| 8,586,103 B2 | 11/2013 | Li | |
| 8,688,385 B2 | 4/2014 | Mrazek | |
| 9,474,728 B2 | 10/2016 | Lederman | |
| 9,636,408 B2 | 5/2017 | Nebuloni | |
| 9,918,948 B2 | 3/2018 | Lederman | |
| 9,956,188 B2 | 5/2018 | Nebuloni | |
| 10,117,936 B2 | 11/2018 | Nebuloni | |
| 10,322,094 B2 | 6/2019 | Nebuloni | |
| 10,357,465 B2 | 7/2019 | Lederman | |
| 10,722,478 B2 | 7/2020 | Lederman | |
| 10,736,859 B2 | 8/2020 | Nebuloni | |
| 10,864,175 B2 | 12/2020 | Nebuloni | |
| 10,864,176 B2 | 12/2020 | Nebuloni | |
| 11,026,898 B2 | 6/2021 | Lederman | |
| 2001/0046988 A1 | 11/2001 | Iglehart | |
| 2003/0077227 A1 | 4/2003 | Dugger | |
| 2003/0077297 A1 | 4/2003 | Chen | |
| 2005/0059656 A1* | 3/2005 | Kristal | A61P 25/28 |
| | | | 514/225.8 |
| 2005/0096327 A1 | 5/2005 | Caprathe | |
| 2005/0181041 A1 | 8/2005 | Goldman | |
| 2005/0203191 A1 | 9/2005 | McDonald | |
| 2006/0073189 A1 | 4/2006 | Pinney | |
| 2007/0141144 A1 | 6/2007 | Roberts | |
| 2007/0196364 A1 | 8/2007 | Krishnamurthy | |
| 2008/0146672 A1 | 6/2008 | Denton | |
| 2009/0054403 A1 | 2/2009 | Woiwode | |
| 2009/0069267 A1 | 3/2009 | Abrams | |
| 2009/0098200 A1 | 4/2009 | Krayz | |
| 2009/0275541 A1 | 11/2009 | Sullivan | |
| 2010/0021507 A1 | 1/2010 | Bunick | |
| 2010/0098832 A1 | 4/2010 | Venkatesh | |
| 2010/0247586 A1 | 9/2010 | Hugerth | |
| 2010/0247649 A1 | 9/2010 | Palaparthi | |
| 2010/0266682 A1 | 10/2010 | Davar | |
| 2011/0062614 A1 | 3/2011 | Suenaga | |
| 2011/0068511 A1 | 3/2011 | Sowden | |
| 2011/0124656 A1 | 5/2011 | Lederman | |
| 2011/0319389 A1 | 12/2011 | Lederman | |
| 2012/0101154 A1 | 4/2012 | Lederman | |
| 2012/0232159 A1 | 9/2012 | Lederman | |
| 2013/0165511 A1 | 6/2013 | Lederman | |
| 2014/0171515 A1 | 6/2014 | Lederman | |
| 2014/0336264 A1 | 11/2014 | Nebuloni | |
| 2015/0065581 A1 | 3/2015 | Lederman | |
| 2016/0030576 A1 | 2/2016 | Nebuloni | |
| 2017/0065538 A1 | 3/2017 | Lederman | |
| 2017/0239195 A1 | 8/2017 | Nebuloni | |
| 2017/0281568 A1 | 10/2017 | Lederman | |
| 2018/0193288 A1 | 7/2018 | Lederman | |
| 2018/0344668 A1 | 12/2018 | Nebuloni | |
| 2019/0022030 A1 | 1/2019 | Nebuloni | |
| 2019/0022031 A1 | 1/2019 | Nebuloni | |
| 2019/0282517 A1 | 9/2019 | Nebuloni | |
| 2019/0336458 A1 | 11/2019 | Lederman | |
| 2019/0358177 A1 | 11/2019 | Lederman | |
| 2021/0038538 A1 | 2/2021 | Nebuloni | |
| 2021/0093585 A1 | 4/2021 | Nebuloni | |

FOREIGN PATENT DOCUMENTS

| | | | | |
|---|---|---|---|---|
| WO | WO-9918937 A1 * | 4/1999 | | A61K 9/2009 |
| WO | WO1999018937 | 4/1999 | | |
| WO | WO1999058115 | 11/1999 | | |
| WO | WO2001012174 | 2/2001 | | |
| WO | WO2001012175 | 2/2001 | | |
| WO | WO2001089476 | 11/2001 | | |
| WO | WO2004035021 | 4/2004 | | |
| WO | WO2004039320 | 5/2004 | | |
| WO | WO2005051297 | 6/2005 | | |
| WO | WO2007038620 | 4/2007 | | |
| WO | WO2008137923 | 11/2008 | | |
| WO | WO2009002770 | 12/2008 | | |
| WO | WO2009089494 | 7/2009 | | |
| WO | WO2011062614 | 5/2011 | | |
| WO | WO-2011062614 A1 * | 5/2011 | | A61K 31/015 |
| WO | WO2012137054 | 10/2012 | | |
| WO | WO2013188847 | 6/2013 | | |
| WO | WO2013188847 | 12/2013 | | |
| WO | WO2014145156 | 3/2014 | | |
| WO | WO-2014071134 A1 * | 5/2014 | | C07D 311/30 |
| WO | WO2014145156 | 9/2014 | | |
| WO | WO-2014145156 A2 * | 9/2014 | | A61K 31/137 |
| WO | WO2016044796 | 3/2016 | | |

OTHER PUBLICATIONS

Balant et al., "Prodrugs for the improvement of drug absorption via different routes of administration," European Journal of Drug Metabolism and Pharmacokinetics, 15(2):143-153 (1990).

Balasubramaniam et al., "Effects of superdisintegrants on dissolution of cationic drugs,"Dissolution Technologies, 18-25 (2008).

Barnes et al., "Brainstem noradrenergic system depression by cyclobenzaprine," Neuropharmacology, 19:221-224 (1980).

Bennett et al., "A comparison of cyclobenzaprine and placebo in the management of fibrositis: A double-blind controlled study," Arthritis Rheum., 31:1535-1542 (1988).

Bhowmik et al., "Fast dissolving tablet: an overview," Journal of Chemical and Pharmaceutical Research, 1:163-177 (2009).

Bingshen, et al., "Pharmacy of Chinese Materia Medica," Chinese Medicine Science and Technology Publishing House, 384-387 (Feb. 28, 2018) (English Translation).

Bundgaard, "Novel chemical approaches in prodrug design," Drugs of the Future, 16:443-458.

Canevelli et al., "Sundowning in Dementia: Clinical Relevance, Pathophysiological Determinants, and Therapeutic Approaches," Frontiers in Medicine, 3:1-7 (2016).

Cantini et al., "[Fluoxetin combined with cyclobenzaprine in the treatment of fibromyalgia]," Minerva Med., 85:97-100 (1994) (Abstract in English).

Cavaljuga et al., "Therapeutic effects of two antidepressant agents in the treatment of posttraumatic stress disorder (PTSD)," Bosnian Journal of Basic Medical Sciences, 3(2):12-16 (2003).

Chaves et al., "Protein aggregation containing beta-amyloid, alpha-synuclein and hyperphosphorylated tau in cultured cells of hippocampus, substantia nigra and locus coeruleus after rotenone exposure," BMC Neuroscience, 11:144, pp. 1-10 (2010).

Cimolai, "Cyclobenzaprine: a new look at an old pharmacological agent," Expert Review of Clinical Pharmacology, 2(3):255-263 (2009).

Commissiong et al., "Cyclobenzaprine: a possible mechanism of action for its muscle relaxant effect," Canadian Journal of Physiology and Pharmacology, 59(1):37-44 (1981).

Cotton et al., "Cyclobenzaprine hydrochloride," Anal Profiles Drug Subs, 17:41-72 (1988).

Cummings et al., "Agitation in cognitive disorders: International Psychogeriatric Association provisional consensus clinical and research definition," International Psychogeriatrics, 27:7-17 (2014).

Cummings et al., "Alzheimer's disease drug development pipeline: 2017," Alzheimer's Dement (NY), 3(3):367-384 (2017).

Cyclobenzaprine (Flexeril), eMedExpert.com—Facts, Oct. 5, 2008 (Oct. 5, 2008), pp. 1-2,URL:http://www.emedexpert.com/facts/cyclobenzaprine-facts.shtml.

Donnelly, "Pharmacologic treatment approaches for children and adolescents with posttraumatic stress disorder," Child Adolescent Psychiatry Clinical North America, 12(2):251-269 (2003).

(56) References Cited

OTHER PUBLICATIONS

Drye et al., "Citalopram for agitation in Alzheimer's disease: design and methods," Alzheimer's & Dementia, 8(2):121-130 (2012).
Esiri, "The basis for behavioural disturbances in dementia," The Journal of Neurology, Neurosurgery, and Psychiatry, 61(2):127-130 (1996).
Evans, "Expert opinion: posttraumatic headaches among United States soldiers injured in Afghanistan and Iraq," Headache, 48(8):1216-1225 (2008).
Falcon et al., "Tricyclics: possible treatment for posttraumatic stress disorder," Journal of Clinical Psychiatry, 46(9):385-388 (1985).
Fibromyalgia: medications for fibromyalgia. Jun. 12, 2008 (3 pages).
Fietta et al., "Fibromyalgia and psychiatric disorders," Acta Biomed, 78(2):88-95 (2007).
Fleisher, et al., "Clinical predictors of progression to Alzheimer disease in amnestic mild cognitive impairment," Neurology, 68(19):1588-1595 (2007).
Folstein et al., "Mini-mental state". A practical method for grading the cognitive state of patients for the clinician, Journal of Psychiatric Research, 12(3):189-198 (1975).
Fossaluzza et al., "Combined therapy with cyclobenzaprine and ibuprofen in primary fibromyalgia syndrome," International Journal of Pharmacology Research, 12:99-102 (1992).
Gai et al., "Bioavailability of a controlled-release cyclobenzaprine tablet and influence of a high fat meal on bioavailability," International Journal of Clinical Pharmacology and Therapeutics, 47(4):269-274 (2009).
Gareri et al., "Use and safety of antipsychotics in behavioral disorders in elderly people with dementia," Journal of Clinical Psychopharmacology, 34(1): 109-123 (2014).
Godfrey, "A guide to the understanding and use of tricyclic antidepressants in the overall management of fibromyalgia and other chronic pain syndromes," Archives of Internal Medicine, 156:1047-1052 (1996).
Greenblatt et al., "Use of Antipsychotics for the Treatment of Behavioral Symptoms of Dementia," Journal of Clinical Pharmacology, 56(9):1048-57 (2016).
Honda et al., "Tricyclic analogs cyclobenzaprine, amitriptyline and cyproheptadine inhibit the spinal reflex transmission through 5-HT(2) receptors," European Journal of Pharmacology, 458(1-2):91-99 (2003).
Hucker et al., "Metabolism of cyclobenzaprine in the dog," Drug Metabolism & Disposition, 6(2):184-192 (1978).
Hucker et al., Physiological disposition and metabolism of cyclobenzaprine in the rat, dog, rhesus monkey, and man Drug Metabolism & Disposition, 6:659-672 (1978).
Hucker et al., "Plasma levels and bioavailability of cyclobenzaprine in human subjects," Journal of Clinical Pharmacology, 17:719-727 (1977).
Jorgensen et al., "Pharmacokinetics of amitriptyline infused intravenously in man," European Journal of Clinical Pharmacology, 10:337-341 (1976).
Kaivosaari et al., "N-glucuronidation of drugs and other xenobiotics by human and animal UDP-glucuronosyltransferases," Xenobiotica., 41:652-669 (2011).
Kar, " Behavioral and psychological symptoms of dementia and their management," Indian Journal of Psychiatry, 51(Suppl 1):S77-D86 (2009).
Katz et al., "Cyclobenzaprine in the treatment of acute muscle spasm: review of a decade of clinical experience," Clinical Therapeutics, 10(2):216-228 (1988).
Kerner et al., "Obstructive Sleep Apnea is Linked to Depression and Cognitive Impairment: Evidence and Potential Mechanisms," American Journal of Geriatric Psychiatry, 24(6):496-508 (2016).
Kobayashi et al., "Cyclobenzaprine, a centrally acting muscle relaxant, acts on descending serotonergic systems," European Journal of Clinical Pharmacology, 311:29-35 (1996).
Macedo et al., "Is Sleep Disruption a Risk Factor for Alzheimer's Disease?," Journal of Alzheimer's Disease, 58(4):993-1002 (2017).

McCurry et al., "Increasing walking and bright light exposure to improve sleep in community-dwelling persons with Alzheimer's disease: results of a randomized, controlled trial," Journal of the American Geriatric Society, 59(8):1393-402 (2011).
Miller et al., "Management of fibromyalgia, a distinct rheumatologic syndrome," Clinical Pharmacy, 6(10):778-786 (1987).
Moldofsky et al., "Effects of bedtime very low dose cyclobenzaprine on symptoms and sleep physiology in patients with fibromyalgia syndrome: a double-blind randomized placebo-controlled study," Journal of Rheumatology, 38(12):2653-2663 (2011).
Moldofsky et al., "Relationship of Sleep Quality and Fibromyalgia Outcomes in a Phase 2b Randomized, Double-Blind, Placebo-Controlled Study of Bedtime, Rapidly Absorbed, Sublingual Cyclobenzaprine (TNX-102 SL)," Arthritis Rheumatology, 67 (suppl 10) (2015).
Narang et al., "Sublingual mucosa as a route for systemic drug delivery," International Journal of Pharma Sciences, 3:18-22 (2011).
Ohrem et al., "Why is mannitol becoming more and more popular as a pharmaceutical excipient in solid dosage forms?," Pharmaceutical Development and Technology, 19(3):257-262 (2014).
Pae, et al., "The relationship between fibromyalgia and major depressive disorder: a comprehensive review," Current Medical Research and Opinion, 24(8):2359-2371 (2008).
Pearlitol® Product Information (website:www.roquette.conn/-/nnedia/sannple-sharepoint-libraries/nnarconnonline---pharnna/ roquette-pharnna-oral-dosage-brochure- pearlitol-nnannitol.pdf) (2012) (22 pages).
Peters et al., "Citalopram for the treatment of agitation in Alzheimer dementia: genetic influence," Journal of Geriatric Psychiatry and Neurology; 29(2):59-64 (2016).
Proitsi et al., "Association of serotonin and dopamine gene pathways with behavioral subphenotypes in dementia," Neurobiology of aging, 33(4):791-803 (2012).
Protocol Registration Receipt Jun. 26, 2012, "Comparative bioavailability of sublingual TNX-102, oral and intravenous cyclobenzaprine in healthy adults" 4 pages.
Razaghi et al., "Investigation of cyclobenzaprine hydrochloride release from oral osmotic delivery systems containing a water-swellable polymer," Drug Dev. Ind. Pharma., 28:631-639.
Rizzi et al.,"Cyclic alternating pattern: a new marker of sleep alteration in patients with fibromyalgia?," Journal of Rheumatology, 31:1193-1199 (2004).
Rosa et al, "Automatic detection of cyclic alternating pattern (CAP) sequences in sleep: preliminary results," Clinical Neurophysiology, 110:585-592 (1999).
Rosa et al., "Somatic treatments for mood disorders," Neuropsychopharmacology, 37(1):102-116 (2013).
Rose et al., "Correlates among nocturnal agitation, sleep, and urinary incontinence in dementia," American Journal of Alzheimer's Disease Other Dementia, 30(1):78-84 (2015).
Ross et al., "Protein aggregation and neurodegenerative disease," Nature Medicine, 10(Suppl):S10-7 (2004).
RX-s.net, https://web.archive.org/web/20060516153148/http:1/rx-s.net/weblog/more/cyclobenzaprine_flexerilreg/ [retrieved on Mar. 12, 2013], from 2006 (2 pages).
Sachdev et al., "DSM-5 and Mental Disorders in Older Individuals: An Overview," Harvard Review of Psychiatry, 23(5):320-328 (2015).
Santandrea et al., "A double-blind crossover study of two cyclobenzaprine regimens in primary fibromyalgia syndrome," Journal of International Medical Research, 21:74-80 (1993).
Schneider et al., "Efficacy and adverse effects of atypical antipsychotics for dementia: meta-analysis of randomized, placebo-controlled trials," American Journal of Geriatric Psychiatry, 14(3):191-210 (2006).
Schneider et al., "Risk of death with atypical antipsychotic drug treatment for dementia: meta-analysis of randomized placebo-controlled trial," JAMA, 294(15):1934-43 (2005).
Shih et al., "Sundown Syndrome, Sleep Quality, and Walking Among Community-Dwelling People With Alzheimer Disease," Journal of the American Medical Directors Association, 18(5), 396-401 (2017).
Shukla et al., "Mouth dissolving tablets I: an overview of formulation," Technology Scientia Pharmaceutica, 76:309-326 (2009).

(56) References Cited

OTHER PUBLICATIONS

Siddegowda et al., "Cyclo-benzaprinium chloride," Acta Crystallographica, Sect. E Struct. Rep. Online. Jul. 1, 2011; 67(Pt 7): o1846 (Abstract only) (2 pages).
Sura et al., "Dysphagia in the elderly: management and nutritional considerations," Clinical Interventions in Aging, 7:287-298 (2012).
Sutfin et al., "The analysis and disposition of imipramine and its active metabolites in man," Psychopharmacology (Berl.), 82:310-317 (1984).
Terzano et al., "Atlas, rules, and recording techniques for the scoring of cyclic alternating pattern sleep," Sleep Medicine, 3:187-199 (2002).
Terzano et al., "Polysomnographic analysis of arousal responses in obstructive sleep apnea syndrome by means of the cyclic alternating pattern," Journal of Clinical Neurophysiology, 13:145-155 (1996).
Thomas et al., "Sleep as a window into the world of fibromyalgia syndrome," Journal of Rheumatology, 38:2499-2500 (2011).
Till et al., "Evidence for route dependent biotransformation of cyclobenzaprine hydrochloride," Biopharmaceutics & Drug Disposition, 3:19-28 (1982).
Trzepacz et al., "Validation of the Delirium Rating Scale-revised-98: comparison with the delirium rating scale and the cognitive test for delirium," Journal of Neuropsychiatry and Clinical Neuroscience, 13(2):229-242 (2001).
Vaddady et al., "In vitro pharmacokinetic/pharmacodynamic models in anti-infective drug development: focus on TB," Future Medicinal Chemistry, 2:1355-1369 (2010).
Walsh, "Drugs Used to Treat Insomnia in 2002: Regulatory-Based Rather Than Evidence-Based Medicine," Sleep, 27(8):1441-1442 (2004).
Wang et al., "Identification of human liver cytochrome P450 isoforms involved in the in vitro metabolism of cyclobenzaprine," Drug Metabolism and Disposition, 24:786-791 (1996).
Wang et al., "Prazosin for the treatment of behavioral symptoms in patients with Alzheimer disease with agitation and aggression," American Journal of Geriatric Psychiatry, 17(9):744-751 (2009).
Way et al., "Isotope dilution gas chromatographic-mass spectrometric measurement of tricyclic antidepressant drugs. Utility of the 4-carbethoxyhexafluorobutyryl derivatives of secondary amines," Journal of Analytical Toxicology, 22:374-382 (1998).
Weaver et al., "An instrument to measure functional status outcomes for disorders of excessive sleepiness," Sleep, 20(10):835-843 (1997).
Weintraub et al., "Pharmacologic interventions for psychosis and agitation in neurodegenerative diseases: evidence about efficacy and safety," Psychiatric Clinicals in North America, 28(4):941-983 (2005).
Williamson et al., "Pharmacological interventions for agitation in patients with traumatic brain injury: protocol for a systematic review and meta-analysis," Systemic Review, 5(1):193 (2016).
Wilson et al., "PTSD has Unreliable Diagnotic Criteria," Psychiatric Times, 26(7):4 pages (2009).
Winchell et al., "Cyclobenzaprine pharmacokinetics, including the effects of age, gender, and hepatic insufficiency," Journal of Clinical Pharmacology, 42:61-69 (2002).
Wong et al., "Potential interference of cyclobenzaprine and norcyclobenzaprine with HPLC measurement of amitriptyline and nortriptyline: resolution by GC-MS analysis," Journal of Analytical Toxicology, 19:218-224 (1995).
World Health Organization Dementia Fact Sheet (2017) (5 pages).
Xie et al., "Sleep drives metabolite clearance from the adult brain," Science, 342(6156):373-377 (2013).
Yoshinari et al., "Moisture induced polymorphic transition of mannitol and its morphological transformation," International Journal of Pharmaceutics, 247(1-2):69-77 (2002).
Yoshinari et al., "The improved compaction properties of mannitol after a moisture-induced polymorphic transition," International Journal of Pharmaceutics, 258(1-2):121-131 (2003).
Zelapar Full Prescribing Information, Cardinal Health, Inc., Valeant Pharmaceuticals North America, Jul. (2006) (2 pages).
Bjellanda et al., "The validity of the Hospital Anxiety and Depression Scale. An updated literature review," Journal of Psychosomatic Research, 52:69-77 (2002).
Experimental Report, Batch No. CYB_GAL_001, dated Aug. 24, 2020 (13 pages).
Gibson, "Pharmaceutical Preformulation and Formulation", 2nd Edition, New York, 231-234 (2009) (8 pages).
Goodnick et al., "Psychotropic treatment of chronic fatigue syndrome and related disorders," Journal of Clinical Psychiatry, 54(1):13-20 (1993).
Harris et al, "Cyclobenzarprine (CBP) is a Potent Antagonist of Serotonin Receptor 2a (5-HT2a) and alpha-2 Adrenergic Receptors: Mechanistic Implications for Promotinh Restorative Sleep in Fibromyalgia Syndrome (FMS)," Arthritis & Rheumatism, 62(10S):abstract 799 (2010).
Hospital Anxiety and Depression Scale Questionnaire (undated) (1 page).
Moldofsky, et al., "A double-blind, randomized, parallel study of the safety, efficacy and tolerability of very low-dosage cyclobenzaprine compared to placebo in subjects with Fibromyalgia," Arthritis & Rheumatology, 46(95):S614 (2002).
Mullin, "Crystallization and Precipitation," Ullman's Encyclopedia of Industrial Chemistry, 6th Edition, vol. 10, London 424-428 (2009) (16 pages).
Razaghi et al., "Investigation of cyclobenzaprine hydrochloride release from oral osmotic delivery systems containing a water-swellable polymer," Drug Development and Industrial Pharmacy, 28(6):695-701 (2002).
Rowe et al., "Handbook of Pharmaceutical Excipients," 6th Edition, London 424-428 (2009) (7 pages).
Bennet et al., "A internet survey of 2,596 people with fibromyalgia," BMC Musculoskeletal Disorders, 8(27):2-12 (2007).
Razaghi et al., "Investigation of cyclobenzaprine hydrochloride release from oral osmotic systems containing a water-swellable polymer," Drug Development and Industrial Pharmacy, 28(6):631-639 (2002).
Razaghi et al., "Release of cyclobenzaprine hydrochloride from osmotically rupturable tablets," Drug Development and Industrial Pharmacy, 28(6):695-701 (2002).
Ullmann's Encyclopedia of Industrial Chemistry, 6th Edition, Weinheim, vol. 10, Chapter 2 (16 Pages) (2003).
Flexeril® (Flexeril (Cyclobenzaprine HCI) Tablets, 2001, C:\N17-821\N17821S045AP1tr.doc (fda.gov)) (9 pages).
Alamo et al., "Evaluation of a patient-centred approach in generalized musculoskeletal chronic pain/fibromyalgia patients in primary care," Patient Education and Counseling, 48(1):23-31 (2002).
Anderson et al., "Evidence-based guidelines for treating depressive disorders with antidepressants: A revision of the 2000 British Association for Psychopharmacology gridelines," Journal of Psychopharmacology, 22(4):343-396 (2008).
Anonymous, "Guideline on clinical investigation of medicinal products in the treatment of depression," European Medical Agency Science Medicines Health, (May 30, 2013) (19 pages).
Aulton, "Pharmaceutics—The Science of Dosage Form Design," Second Edition, Churchill Livingstone, De Montfort University, Leicester, UK (2007).
Baru et al., "Cyclobenzaprine drug assay and cyclobenzaprine-excipient interaction study by chromatography, thermal and spectral analysis," Journal of Pharmaceutical Chemistry & Chemical Science, 1(1):1-9 (2017).
Caley et al., "SSRI efficacy-finding the right dose," Journal of Psychiatric Practice, 8(1):33-40 (2002).
Carette et al., "Comparison of amitriptyline, cyclobenzaprine, and placebo in the treatment of fibromyalgia. A randomized, double-blind clinical trial," Arthritis and Rheumatism, 37(1):32-40 (1994).
Elsner et al., "Newer generation fentanyl transmucosal products for breakthrough pain in opioid-tolerant cancer patients," Clinical Drug Investigation, 31(9): 605-618 (2011).
Hu Xiang Feng et al., "Overview of fibromyalgia syndrome treatment," Chinese Medical Journal of Metallurgical Industry, 23(4):454-456(2006) (Machine Translation).
Iupac Gold Book E02225: "eutectic reaction" (1 page) (2014).

(56) References Cited

OTHER PUBLICATIONS

Katz et al., "A study of sublingual absorption. II. Striated muscle relaxants and neurovegetative blocking agents," Journal of the American Pharmaceutical Association, 44(8):472-476 (1955).
Kim et al., "Tablet Formulation of Eutectic Mixture: Preparation of Tablet Containing Aspirin and Isopropylantipyrine," Yakhak Joeji, 29(4):193-198 (1985) (with English Translation).
Li Xinzhong etal., Handbook of Practical Drug for Residents, the 1st edition, (2009). (Machine Translation).
Lok et al., "The Performance of the Hospital Anxiety and Depression Scale for Screening of Depressive and Anxiety Disorders in Patients with Rheumatoid Arthritis (RA)," Arthritis and Rheumatology, 62(10S):Abstract 1777 (2010) (2 pages).
*Merck & Co., Inc.* v. *Danbury Pharmacal, Inc.*, Civil Action No. 86-588 Mms, U.S. District Court of Delaware, Opinion (Aug. 31, 1988) (32 pages).
Product monograph for Elavil® Amitriptyline Hydrochloride Tablets USP (Jul. 23, 2010) (17 pages).
Shen et al, "The Advance on Studies of Fibromyalgia syndrome," Chinese Journal of Clinical Neurosciences, 20(3):329-334 (2012).
U.S. Appl. No. 13/918,692, filed Jun. 14, 2013, Pending.
U.S. Appl. No. 12/948,828, filed Nov. 18, 2010, Issued, U.S. Pat. No. 9,918,948.
U.S. Appl. No. 15/915,688, filed Mar. 8, 2018, Abandoned.
U.S. Appl. No. 17/951,723, filed Sep. 23, 2022, Abandoned.
U.S. Appl. No. 13/157,270, filed Jun. 9, 2011, Abandoned.
U.S. Appl. No. 14/477,981, filed Sep. 5, 2014, Issued, U.S. Pat. No. 9,474,728.
U.S. Appl. No. 15/266,035, filed Sep. 15, 2016, Abandoned.
U.S. Appl. No. 16/537,170, filed Aug. 9, 2019, Issued, U.S. Pat. 10,722,478.
U.S. Appl. No. 16/903,965, filed Jun. 17, 2020, Pending.
U.S. Appl. No. 13/412,571, filed Mar. 5, 2012, Pending.
U.S. Appl. No. 14/214,433, filed Mar. 14, 2014, Issued, U.S. Pat. No. 9,636,408.
U.S. Appl. No. 15/459,093, filed Mar. 15, 2017, Issued, U.S. Pat. No. 9,956,188.
U.S. Appl. No. 15/941,484, filed Mar. 30, 2018, Issued, U.S. Pat. No. 10,322,094.
U.S. Appl. No. 16/429,852, filed Jun. 3, 2019, Issued, U.S. Pat. No. 10,736,859.
U.S. Appl. No. 14/776,624, filed Sep. 14, 2015, Issued, U.S. Pat. No. 10,117,936.
U.S. Appl. No. 15/511,287, filed Mar. 15, 2017, Issued, U.S. Pat. No. 10,357,465.
U.S. Appl. No. 16/140,090, filed Sep. 24, 2018, Issued, U.S. Pat. No. 10,864,175.
U.S. Appl. No. 16/140,105, filed Sep. 24, 2018, Issued, U.S. Pat. No. 10,864,176.
U.S. Appl. No. 16/518,338, filed Jul. 22, 2019, Issued, U.S. Pat. No. 11,026,898.
U.S. Appl. No. 17/082,949, filed Oct. 28, 2020, Pending.
U.S. Appl. No. 17/121,547, filed Dec. 14, 2020, Allowed.
U.S. Appl. No. 17/269,106, filed Feb. 17, 2021, Pending.
U.S. Appl. No. 17/226,058, filed Apr. 8, 2021, Pending.
U.S. Appl. No. 18/265,525, filed Jun. 6, 2023, Pending.
Celik et al., "Efficacy of Paroxetine and Amitriptyline in Post-traumatic Stress Disorder: An Open-label Comparative Study," Bulletin of Clinical Sychopharrnacology, 21(3):179-185 (2011).
Li Jianhong, "New Drug Handbook," Jiangxi Science and Technology Press, 2nd Edition, pp. 81-82 (2005) (1 page) (English Translation).

\* cited by examiner

CYCLOBENZAPRINE TREATMENT FOR AGITATION, PSYCHOSIS AND COGNITIVE DECLINE IN DEMENTIA AND NEURODEGENERATIVE CONDITIONS

This application claims priority to and benefit from U.S. Provisional Patent Application 62/597,284, filed Dec. 11, 2017, the contents and disclosures of which are incorporated herein by reference in their entirety.

FIELD OF THE DISCLOSURE

This application relates to methods for the treatment or prevention of agitation, psychosis and/or cognitive decline and associated symptoms thereof in dementia or in a neurodegenerative condition, and related pharmaceutical compositions. Of particular interest are pharmaceutical compositions comprising cyclobenzaprine, alone, or in combination with one or more of a cholinesterase inhibitor, an N-methyl-D-aspartate receptor antagonist, an antidepressant, an anti-anxiety agent, an antipsychotic agent, an anticonvulsant or mood stabilizer, an anti-amyloid agent, or an anti-tau agent.

BACKGROUND OF THE DISCLOSURE

Cyclobenzaprine, or 3-(5H-dibenzola[a,d]cyclohepten-5-ylidene)-N,N-dimethyl-1 propanamine, was first approved by the U.S. Food and Drug Administration in 1977 for the treatment of acute muscle spasms of local origin. (Katz and Dube, 1988). Subsequent studies have shown that it is a potent $5-HT_{2A}$ and $\alpha_{1A}$ antagonist which improves restorative sleep in neuropsychiatric disorders and fibromyalgia through antagonism of serotonergic-2A ($5-HT_{2A}$) and alpha-adrenergic-1A ($\alpha_{1A}$) receptors during the sleep period (Moldofsky et al., 2011, Moldofsky et al., 2015).

The utility of a very low dose cyclobenzaprine as an agent for improving the quality of sleep, as a sleep deepener, or for treating sleep disturbances has previously been investigated. The very low dosage regimen was viewed as particularly useful in treating sleep disturbances caused by, exacerbated by or associated with fibromyalgia syndrome, prolonged fatigue, chronic fatigue, chronic fatigue syndrome, a sleep disorder, a psychogenic pain disorder, chronic pain syndrome (type II), the administration of a drug, autoimmune disease, stress or anxiety or for treating an illness caused by or exacerbated by sleep disturbances, and symptoms of such illness, generalized anxiety disorder, and post-traumatic stress disorder (PTSD). See U.S. Pat. App No. US20110124656A1, and U.S. Pat. Nos. 6,395,788 and 6,358,944, incorporated herein by reference.

Dementia, caused by diseases such as Alzheimer's Disease (AD), is a neurological syndrome that affects nearly 47 million people worldwide with the number of cases expected to triple by 2050 (WHO 2017). Neurodegenerative conditions associated with symptoms of dementia are also widely prevalent (Chaves 2010; Weintraub 2005; Diaz-Olavarrieta C. 1999; Williamson 2016). Sleep disruptions associated with blood-brain barrier hyperpermeability and neuroinflammation can contribute to the development of dementia (Kerner and Roose 2016) and amyloid-beta deposition in AD (Macedo 2017). Restoring sleep has been shown to improve the clearance of amyloid-beta protein (Xie et al, 2013).

Behavioral and psychological symptoms of dementia (BPSD) include agitation, a large group of behaviors which has a reported prevalence of nearly 56% in dementia patients and psychosis, prevalent in 50% of patients. BPSD is also associated with a more rapid rate of cognitive decline and greater impairment in activities of daily living (Kar 2009). Agitation is strongly associated with activation of the stress response system and accompanying disturbances in sleep, both under the neuromodulatory influence of monoaminergic pathways to the prefrontal cortex (PFC). Neurobiological evidence points to abnormalities in prefrontal cortex (PFC) $5-HT_{2A}$ and $\alpha_{1A}$ receptors in dementias with agitation, and antagonists of these receptors have been shown to reduce such disruptive agitation (Assal et al., 2004; Esiri, 1996; Wang et al., 2009).

While several second-generation antipsychotics (SGAs) potently antagonize $5-HT_{2A}$ and $\alpha_{1A}$ receptors and reduce agitation and associated symptoms in dementia, the SGA class has a high side effect burden and may increase mortality in patients with dementia (Schneider et al., 2006, Greenblatt and Greenblatt 2016, Gareri 2014). Agitation is also known to be associated with various neurodegenerative conditions (Chaves 2010; Weintraub 2005; Diaz-Olavarrieta C. 1999; Williamson 2016). Thus, there is a significant unmet medical need for an efficacious treatment with a safety profile suitable for long-term treatment of agitation and associated symptoms in dementia and/or neurodegenerative conditions.

International Publication No. WO2013188847, incorporated herein by reference, discloses a low dose, sublingual formulation of cyclobenzaprine (TNX-102 SL) that has rapid transmucosal absorption to blood and uniquely reduced production of a long half-life active metabolite, norcyclobenzaprine, due to bypass of first-pass hepatic metabolism. In the elderly population, at oral doses of 5 mg (IR tablets three times daily [TID]), cyclobenzaprine does not appear to cause excessive drowsiness or impair performance on cognitive tasks.

Clinical studies with TNX-102 SL in amounts up to 5.6 mg, taken sublingually at bedtime for 12 weeks or longer, have demonstrated that TNX-102 SL was well tolerated by patients with fibromyalgia (FM) and post traumatic stress disorder (PTSD) (Clinical Trials NCT02277704, NCT01903265 and NCT02436096). There were no serious or unexpected central nervous system (CNS)-related adverse events. The systemic adverse events reported with TNX-102 SL are consistent with those described in the marketed cyclobenzaprine product labeling.

TNX-102 SL comprises cyclobenzaprine which retains therapeutically important biological activities including $5-HT_{2A}$ and $\alpha_{1A}$ receptor antagonism, even in nanomolar concentration ranges (see WO2013188847), and has a high safety and tolerability profile at low doses. The cyclobenzaprine sublingual (SL) formulation described herein confers an additional advantage in the elderly population in which swallowing difficulties are common (Sura et al 2012).

SUMMARY OF THE DISCLOSURE OF THE APPLICATION

In one aspect the application discloses a method for treating or preventing agitation, psychosis, and/or cognitive decline and associated symptoms thereof in dementia or in a neurodegenerative condition. The symptoms may be a sleep disturbance or a non-sleep disturbance associated with dementia and/or a neurodegenerative condition. The method comprises administering to a subject suffering from or at risk for developing agitation, psychosis, and/or cognitive decline and associated symptoms thereof in dementia or in a neurodegenerative condition, a pharmaceutical composition comprising a therapeutically effective amount of cyclobenzaprine and a pharmaceutically acceptable carrier. In some embodiments, the composition may be administered at a dose between 0.1 mg to 30 mg cyclobenzaprine/day or at a dose between 0.1 mg to 20 mg cyclobenzaprine/day. In some embodiments, the composition may be administered at a dose less than 10 mg cyclobenzaprine/day or less than 5 mg cyclobenzaprine/day. In preferred embodiments, the composition may be administered at a dose of about 5.6 mg cyclobenzaprine/day. In some embodiments, the composition may be administered at a dose of about 2.8 mg cyclobenzaprine/day. The composition may be administered daily or once daily. In some embodiments, the composition is administered simultaneously as two dosage units of 2.8 mg cyclobenzaprine each. In some embodiments, the composition is administered simultaneously as two dosage units, wherein the combined amount of cyclobenzaprine in the two dosage units is about 5.6 mg.

In some embodiments, the method may further include administering sequentially or concurrently one or more of an agent selected from the group consisting of cholinesterase inhibitor, an N-methyl-D-aspartate (NMDA) receptor antagonist, an antidepressant, an anti-anxiety agent, an antipsychotic agent, an anticonvulsant or mood stabilizer, an anti-amyloid agent, and an anti-tau agent. In some embodiments, the cholinesterase inhibitor is donepezil, rivastigmine, galantamine, or tacrine. In some embodiments, the NMDA receptor antagonist is amantadine or memantine. In some embodiments, the antidepressant is citalopram, fluoxetine, paroxetine, or sertraline. In some embodiments, the anti-anxiety agent is lorazepam, oxazepam, or buspirone. In some embodiments, the antipsychotic agent is quetiapine, trazodone, promazine, aripiprazole, ziprasidone, olanzapine, or risperidone. In some embodiments, the anticonvulsant or mood stabilizer is carbamazepine, divalproex, or dextromethorphan. In some embodiments, the anti-amyloid agent is bapineuzumab, solanezumab, or verubecestat. In some embodiments, the anti-amyloid agent and/or anti-tau agent is one or more of the agents as described by Cummings et al. incorporated herein by reference (Cummings, 2017). In some embodiments, the method may further entail administering sequentially or concurrently, a somatic treatment to the subject.

In some embodiments, the pharmaceutical composition of the application is formulated for sublingual, buccal, oral, suppository, intravenous, intramuscular, subcutaneous, inhalational, intranasal, thin film, transdermal, parenteral, rectal, or vaginal administration. In some embodiments, the pharmaceutical composition is administered in combination with psychotherapeutic, behavioral or environmental intervention. In some embodiments, the pharmaceutical composition is administered sublingually, buccally, orally, in a suppository, intravenously, intramuscularly, subcutaneously, inhalationally, intranasally, in a thin film, transdermally, parenterally, rectally, or vaginally.

In another aspect, the application discloses a pharmaceutical composition comprising a therapeutically effective amount of cyclobenzaprine in combination with one or more agents selected from the group consisting of a cholinesterase inhibitor, an N-methyl-D-aspartate (NMDA) receptor antagonist, an antidepressant, an anti-anxiety agent, an antipsychotic agent, or an anticonvulsant or mood stabilizer, an anti-amyloid agent, and an anti-tau agent. The amount of cyclobenzaprine in the pharmaceutical composition may be any of the following: between 0.1 mg to 30 mg; between 0.1 mg to 20 mg; less than 10 mg; less than 5 mg; about 5.6 mg; or about 2.8 mg. The pharmaceutical composition may be administered daily or once daily.

In yet another aspect, the application discloses a method for selecting an effective dose of cyclobenzaprine to be administered to a subject suffering from or at risk for developing agitation, psychosis and/or cognitive decline and associated symptoms thereof in dementia or in a neurodegenerative condition. The method comprises obtaining a genetic sample from said subject, using said sample to determine the CYP3A, CYP1A2, CYP3A4, or CYP2D6 genotype of said subject, and selecting a therapeutically effective dose of cyclobenzaprine based on that genotype. The CYP3A, CYP1A2, CYP3A4 or CYP2D6 genotype may be determined, for example, by using a gene chip or a PCR technique to identify the alleles of one or more of the genes. Different CYP alleles metabolize cyclobenzaprine at different rates. For individuals having a cytochrome allele known to metabolize cyclobenzaprine more quickly, a higher dose of cyclobenzaprine shall preferably be administered. For individuals having an isoform known to metabolize cyclobenzaprine more slowly, a lower dose of cyclobenzaprine should preferably be administered.

DETAILED DESCRIPTION

Unless otherwise defined herein, scientific and technical terms used in this application shall have the meanings that are commonly understood by those of ordinary skill in the art. In case of conflict, the present specification, including definitions, will control.

Throughout this specification and embodiments, the word "comprise," or variations such as "comprises" or "comprising," will be understood to imply the inclusion of a stated integer or group of integers but not the exclusion of any other integer or group of integers.

The term "including" or "includes" is used to mean "including but not limited to." "Including" and "including but not limited to" are used interchangeably.

Any example(s) following the term "e.g." or "for example" is not meant to be exhaustive or limiting.

Unless otherwise required by context, singular terms shall include pluralities and plural terms shall include the singular.

The articles "a", "an" and "the" are used herein to refer to one or to more than one (i.e., to at least one) of the grammatical object of the article.

Notwithstanding that the disclosed numerical ranges and parameters are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g., 1 to 6.1, and ending with a maximum value of 10 or less, e.g., 5.5 to 10.

Where aspects or embodiments are described in terms of a Markush group or other grouping of alternatives, the present application encompasses not only the entire group listed as a whole, but each member of the group individually and all possible subgroups of the main group, and also the main group absent one or more of the group members. The present application also envisages the explicit exclusion of one or more of any of the group members in the embodimented disclosure.

Exemplary methods and materials are described herein, although methods and materials similar or equivalent to those described herein can also be used in the practice or testing of the various aspects and embodiments. The materials, methods, and examples are illustrative only and not intended to be limiting.

Definitions

In order that the disclosure may be more readily understood, certain terms are first defined. These definitions should be read in light of the remainder of the disclosure as understood by a person of ordinary skill in the art. Unless defined otherwise, all technical and scientific terms used herein have the same meaning as commonly understood by a person of ordinary skill in the art. Additional definitions are set forth throughout the detailed description.

In one aspect the application discloses a method for treating or preventing agitation, psychosis and/or cognitive decline and associated symptoms thereof in dementia or in a neurodegenerative condition.

The method comprises administering to a subject in need or at risk thereof, a pharmaceutical composition comprising a therapeutically effective amount of cyclobenzaprine and a pharmaceutically acceptable carrier. The symptom may be a sleep disturbance or a non-sleep disturbance.

As used herein, the term "treat" and its cognates refer to a full or partial amelioration or modulation of agitation, psychosis and/or cognitive decline or at least one discernible symptom thereof in dementia or in a neurodegenerative condition. In some embodiments, "treat" refers to an improvement or amelioration of agitation behaviors as measured in the Cohen Mansfield Agitation Inventory (CMAI) consisting of a diverse group of agitated behaviors, each rated on a multi-point scale of frequency. The CMAI agitation score of a subject may be measured before and after treatment. An improved score is indicative of successful "treatment". (See, for example, Mansfield, 1991). In certain embodiments, "treat" refers to an improvement or amelioration of agitation behaviors as measured in the Modified Alzheimer's Disease Cooperative Study Clinical Global Impression of Change Agitation Domain (mADCS-CGIC-Agitation) Score. The standard ADCS-CGIC rating was modified to better assess aspects relevant to studying agitation in Alzheimer's disease (Drye et al., 2012). The mADCS-CGIC-Agitation rating contains questions related to agitation and an assessment of the Clinician's Impression of Change focused specifically on agitation. In certain embodiments, "treat" and its cognates refers to slowing the progression or reversing the progression of agitation, psychosis and/or cognitive decline and associated symptoms thereof in dementia or in a neurodegenerative condition relative to an untreated control. In some embodiments, "treat" and its cognates refers to inhibiting or reducing the progression of agitation, psychosis and/or cognitive decline and associated symptoms thereof in dementia or in a neurodegenerative condition. In some embodiments, "treat" and its cognates refers to reducing the severity of agitation, psychosis and/or cognitive decline in the subject. In some embodiments, "treat" refers to an improvement in cognition as measured on the Alzheimer's Disease Assessment Scale-Cog (ADAS-Cog), and/or Mini-mental state exam (MMSE). The cognition scores of a subject may be measured before and after treatment. An improved score is indicative of successful "treatment". (See, for example, Fleisher 2007 and Folstein 1975).

As used herein, "prevent" and its cognates refer to delaying the onset or delaying the time of reoccurrence of or reducing the risk of developing agitation, psychosis and/or cognitive decline or an associated symptom thereof in dementia or in a neurodegenerative condition, relative to an untreated control. As used herein, "delaying the time of the reoccurrence" and its cognates refer to delaying the recurrence of agitation, psychosis and/or cognitive decline or an associated symptom thereof in dementia or in a neurodegenerative condition, in an individual susceptible to developing agitation, psychosis and/or cognitive decline or associated symptom thereof in dementia or in a neurodegenerative condition or who has in the past developed such agitation, psychosis and/or cognitive decline or associated symptom relative to an untreated control.

As used herein, the term "agitation" refers to agitation and symptoms of agitation in dementia and/or a neurodegenerative condition and associated symptoms thereof including personality changes, general emotional distress (rapid changes in mood, irritability, and outbursts), anxiety, depression, delusions (firmly held belief in things that are not real), hallucinations (seeing, hearing or feeling things that are not there), excessive motor activity (e.g., pacing, constant movement, rocking, gesturing, pointing fingers, restlessness, performing repetitious mannerisms), checking and rechecking doors or appliances, tearing tissues, uncharacteristic cursing or threatening language. The behavior associated with agitation could be persistent or frequently recurrent for a minimum of two weeks and represents a change from the patient's usual behavior. Further symptoms associated with agitation in dementia and/or a neurodegenerative condition include but are not limited to: delirium, psychosis, cognitive decline, sleep disturbances, insomnia, sundowning, aggression, combativeness, lability of mood, anger, pain, akathysia, compulsions, obsessivity, and urinary incontinence. Other symptoms associated with agitation in dementia and/or a neurodegenerative condition include but are not limited to: verbal aggression (e.g. yelling, speaking in an excessively loud voice, using profanity, screaming, shouting); physical aggression (e.g. grabbing, shoving, pushing, resisting, hitting others, kicking objects or people, scratching, biting, throwing objects, hitting self, slamming doors, tearing things, and destroying property); and significant impairment in one or more of the following: interpersonal relationships, other aspects of social functioning, ability to perform or participate in daily living activities. (Alexopoulos et al. 1998; Gareri 2014; Rose et al. 2015; Shneider et al. 2005, Alzheimer's Association 2004). All other symptoms as defined by the International Psychogeriatric Association Agitation Definition Work Group (Cummings 2014) are included herein. These symptoms are commonly measured by techniques known in the art to the ordinary skilled clinician.

As used herein, the term "sleep disturbance" refers to symptoms including difficulty falling asleep, early morning awakening, nightmares, and sleep of poor quality. The quality of sleep ("sleep disturbance") may be determined, inter alia, by asking the patient if he/she awakened tired or nonrefreshed "never," "seldom," "often or usually," or "always." Replies of "often or usually" or "always" may be scored as positive and other replies as negative. Patients' reports of well-being or relief from "zombie" or "spacey" feelings, feelings of being "run down," and having difficulty concentrating during waking hours are indications of better quality of sleep or deep, refreshing sleep. A rating scale commonly used to assess sleep quality is the Functional Outcomes of Sleep Questionnaire (FOSQ) is described in Weaver et al., (1997).

As used herein, the term "sundowning" refers to neuropsychiatric symptoms and behavioral disturbances occurring in subjects with dementia and/or a neurodegenerative condition at and/or after the time of sunset. Sundowning is associated with disruptions in circadian rhythm. It includes one or more of: anxiety, agitation, aggression, pacing, wandering, resistance, screaming, yelling, visual and auditory hallucinations, sleep disturbances, and confusion. (See for example, Canavelli et al., 2016; Shih, et al, 2017)

As used herein, the term "dementia" refers to a wide range of symptoms associated with a long-term and gradual decline in memory or other thinking skills severe enough to reduce a person's ability to perform everyday activities. It may be associated with inflammation in the brain and parts thereof. Dementia can be associated with one or more of the following: Alzheimer's Disease (AD), Parkinson's Disease (PD), vascular dementia, dementia with Lewy Bodies, mixed dementia, frontotemporal dementia, Creutzfeldt-Jakob Disease (CJD), normal pressure hydrocephalus, Huntington's disease (HD), Wernicke-Korsakoff Syndrome, head injuries, alcoholism, viral or bacterial infection, drug side effects, pneumonia, dehydration, poor nutrition, bladder infections, diabetes, and asthma. A subject at risk of developing dementia includes a subject with mild cognitive impairment. Dementia refers to a condition as defined by DSM-5 guidelines wherein dementia is associated with modest or substantial decline in cognitive function and is referred to as mild or major neurocognitive disorder (Sachdev 2015).

As used herein, the term "neurodegenerative condition" and its cognates refers to diseases which affect the neurons in the human central or peripheral nervous system. The neurodegeneration condition can be associated with abnormal protein aggregation and accumulation, and/or inclusion body formation (Ross and Poirier, 2004; Chaves 2010). For example, the proteins accumulated can be alpha-synuclein, amyloid-beta tau protein. In some embodiments, neurodegenerative conditions may include a condition in which inflammatory cytokines as associated with the pathogenesis of the condition, for example, multiple sclerosis and traumatic brain injury. Neurodegenerative conditions may also include: PD, AD, HD, Amyotrophic lateral sclerosis (ALS), motor neuron disease, schizophrenia, multiple system atrophy, synucleopathies, lewy body dementia, and frontotemporal dementia. See, for example, Chaves 2010; Weintraub 2005; Diaz-Olavarrieta C. 1999; Williamson 2016.

A "patient", "subject", or "individual" are used interchangeably and preferably refer to a human.

As used herein, the term "cyclobenzaprine" refers to cyclobenzaprine or a metabolite thereof, prodrugs of cyclobenzaprine or a metabolite thereof. Metabolites of cyclobenzaprine useful according to the methods of this application are metabolites that have substantially the same or better activity than cyclobenzaprine in alleviating agitation in dementia and/or a neurodegenerative condition or associated symptoms thereof. Cyclobenzaprine metabolites that may be useful according to this application include CBP 10,11-trans-dihydriol, N-desmethyl-2-hydroxycyclobenzaprine, 3-hydroxycyclobenzaprine, N-desmethylcyclobenzaprine, cyclobenzaprine N-oxide, or a chiral isomer of these metabolites. A prodrug of cyclobenzaprine is a derivative of cyclobenzaprine that is metabolized in vivo into the active agent. Prodrugs useful according to this application are those that have substantially the same or better activity than cyclobenzaprine in treating or preventing agitation, psychosis and/or cognitive decline and associated symptoms thereof in dementia or in a neurodegenerative condition. Methods for making prodrugs are readily known in the art (e.g., Balant, et al 1990; Bund-gaard, H et al. 1991 incorporated by reference herein).

As used herein, the term "therapeutically effective amount" of cyclobenzaprine refers to the amount of the compound that treats or prevents, as defined herein, agitation, psychosis and/or cognitive decline and associated symptoms thereof in dementia or in a neurodegenerative condition. A physician can readily determine when symptoms are treated or prevented, for example through clinical observation of a subject, or through reporting of symptoms by the subject or its caregiver during the course of treatment. One skilled in the art can readily determine the amount of a cyclobenzaprine to be administered, by taking into account factors such as the size, weight, age and sex of the subject, the extent of disease penetration or persistence and severity of symptoms, and the route of administration. Generally, a therapeutically effective amount of cyclobenzaprine administered to a subject is between 0.1 mg to 30 mg/day, between 1 to 20 mg/day, less than 10 mg/day, less than 5 mg/day, about 5.6 mg/day, or about 2.8 mg/day. Higher or lower doses are also contemplated.

As used herein, the term "about" refers to a value or parameter that includes (and describes) embodiments that are directed to that value or parameter per se. For example, description referring to "about X" includes description of". As used herein, the term "about" permits a variation of ±10% within the range of the significant digit.

As used herein, the term "agent" refers to a biological or chemical substance or compound that can be used to treat or prevent a condition in the subject. In some embodiments, the agent is an antibody. The condition can be a symptom related to dementia and/or a neurodegenerative condition, including, but not limited to anxiety, psychosis, cognitive decline, mood fluctuations, agitation, convulsions, abnormal neurochemistry that contributes to the pathogenesis of dementia and/or neurodegeneration, protein aggregation and accumulation that contribute to the pathogenesis of dementia and/or the neurodegeneration, e.g., accumulation of amyloid plaques and abnormal tau deposits (see Cummings, 2017).

As used herein, the term "somatic treatments" refers to intervention administered to the subject including but not limited to electroconvulsive therapy, magnetic therapy, transcranial magnetic stimulation, transcranial direct stimulation, cranial electric stimulation, vagus nerve stimulation, epidural electric stimulation, or deep brain stimulation. (See Rosa and Lisanby, 2012).

In some embodiments, the cyclobenzaprine is administered at doses that minimize or lessen any side effects observed at higher doses. These doses include doses of about 5.6 mg/day, less than 5 mg/day, or about 2.8 mg/day. Even lower doses are also contemplated. Generally, cyclobenzaprine therapy can be carried out indefinitely to treat or prevent the agitation, psychosis and/or cognitive decline and associated symptoms thereof in dementia or in a neurodegenerative condition and frequency and/or amount of dosage may be changed as needed. The period of treatment should be as long as necessary to treat or prevent agitation, psychosis and/or cognitive decline and associated symptoms thereof in dementia or in a neurodegenerative condition. In some embodiments, the cyclobenzaprine administered at night-time and at an appropriate dose. The dose may be gradually increased or decreased.

In some embodiments of the application, cyclobenzaprine is administered in combination with one or more of an agent which may further alleviate agitation, psychosis and/or cognitive decline and associated symptoms thereof in dementia or in a neurodegenerative condition. The agents may be administered sequentially or concurrently with the cyclobenzaprine. The agents include one or more of cholinesterase inhibitor, an N-methyl-D-aspartate (NMDA) receptor antagonist, an antidepressant, an anti-anxiety agent, an antipsychotic agent, an anticonvulsant or mood stabilizer, an anti-amyloid agent, and an anti-tau agent. Exemplary cholinesterase inhibitors include, but are not limited to donepezil, rivastigmine, galantamine, or tacrine. Exemplary N-methyl-D-aspartate receptor antagonists include, but are not limited to amantadine or memantine. Exemplary N-antidepressants include, but are not limited to, citalopram, fluoxetine, paroxetine, or sertraline. Exemplary anti-anxiety agents include, but are not limited to, lorazepam, oxazepam, or buspirone. Exemplary antipsychotic agents include, but are not limited to, quetiapine, trazodone, promazine, aripiprazole, ziprasidone, olanzapine, or risperidone. Exemplary anticonvulsant or mood stabilizers include, but are not limited to, carbamazepine, divalproex, or dextromethorphan. Exemplary anti-amyloid agents include, but are not limited to, bapineuzumab, solanezumab, or verubecestat. In some embodiments, the subject is administered about 1.0 mg/day lorazepam to treat breakthrough symptoms of agitation, psychosis and/or cognitive decline and associated symptoms thereof in dementia or in a neurodegenerative condition sequentially or concurrently with the cyclobenzaprine compositions of the disclosure.

In another aspect, the application discloses a pharmaceutical composition. The pharmaceutical composition comprises a therapeutically effective amount of cyclobenzaprine in combination with one or more agents selected from the group consisting of a cholinesterase inhibitor, an N-methyl-D-aspartate (NMDA) receptor antagonist, an antidepressant, an anti-anxiety agent, an antipsychotic agent, an anticonvulsant or mood stabilizer, an anti-amyloid agent, and an anti-tau agent. Generally, the amount of cyclobenzaprine in the pharmaceutical composition is between 0.1 mg to 30 mg, or between 1 mg and 20 mg. Higher or lower doses are also contemplated. In some embodiments, the amount of cyclobenzaprine is less than 10 mg, less than 5 mg, about 5.6 mg, or about 2.8 mg. Even lower amounts are also contemplated. In some embodiments, cyclobenzaprine is combined with at least one of an agent which may further alleviate the symptoms of agitation, psychosis and/or cognitive decline and associated symptoms thereof in dementia or in a neurodegenerative condition. The agent may be administered sequentially or concurrently with the cyclobenzaprine compositions of this invention.

Any suitable route of administration may be employed for providing the subject with the compositions of this application. For example, sublingual, buccal, oral, rectal, vaginal, suppository, parenteral, transdermal, intranasal, inhalational, thin film and the like may be employed as appropriate. The term parenteral as used herein includes subcutaneous, intracutaneous, intravenous, intramuscular, intra-articular, intrasynovial, intrasternal, intrathecal, intralesional and intracranial administration or other infusion techniques. Dosage forms useful in this application may include tablets, such as scored tablets, coated tablets, or orally dissolving tablets; thin films, powders, caplets, capsules (e.g. hard gelatin capsules), troches, dragees, dispersions, suspensions, solutions, patches and the like, including sustained release, extended release, slow release, modified release formulations well known in the art. In preferred embodiments, the dosage form is a sublingual tablet, a sublingual film, a liquid, sublingual powder, or a sublingual spray solution.

As used herein, the term "pharmaceutically acceptable carrier" refers to any diluent or excipient that is compatible with the other ingredients of the formulation, and which is not deleterious to the subject. The pharmaceutically acceptable carrier can be selected on the basis of the desired route of administration, in accordance with standard pharmaceutical practices.

Pharmaceutical compositions of the application for parenteral administration can take the form of an aqueous or nonaqueous solution, dispersion, suspension or emulsion. In preparing pharmaceutical compositions of the application for parenteral administration, cyclobenzaprine can be mixed with a suitable pharmaceutically acceptable carrier such as water, oil (particularly a vegetable oil), ethanol, saline solutions (e.g., normal saline), aqueous dextrose (glucose) and related sugar solutions, glycerol, or glycols such as propylene glycol or polyethylene glycol. Pharmaceutical compositions of the application for parenteral administration preferably contain a water-soluble salt of cyclobenzaprine. Stabilizing agents, antioxidizing agents and preservatives can also be added to the pharmaceutical compositions for parenteral administration. Suitable antioxidizing agents include sulfite, ascorbic acid, citric acid and its salts, and sodium EDTA. Suitable preservatives include benzalkonium chloride, methyl- or propyl-paraben, and chlorbutanol.

In preparing pharmaceutical compositions of the application for sublingual administration, cyclobenzaprine can be combined with one or more solid or liquid inactive ingredients to form tablets, capsules, pills, powders, granules, sprays or other suitable sublingual dosage forms. For example, cyclobenzaprine can be combined with at least one pharmaceutically acceptable carrier such as a solvent, filler, binder, humectant, disintegrating agent, solution retarder, absorption accelerator, wetting agent absorbent or lubricating agent. In one embodiment, cyclobenzaprine is combined with carboxymethylcellulose calcium, magnesium stearate, mannitol or starch, and is formed into tablets by conventional tableting methods. Pharmaceutical compositions suitable for use in the present application are described in, for example, WO2013188847.

Pharmaceutical compositions of the application can be formulated so as to provide sublingual absorption including sublingual tablets, sublingual thin film formulations, sublingual powders, sublingual spray solutions to provide faster absorption than the oral/GI route and to bypass first-pass hepatic metabolism of cyclobenzaprine by cytochrome P-450 3A4 as a CYP3A substrate. Preferably, a controlled-release pharmaceutical composition of the application is capable of releasing cyclobenzaprine into a subject at a desired rate, so as to maintain a substantially constant or desired pharmacological activity for a given period of time, reduce or remove the effect of food on absorption, and to provide elimination of the drug and metabolites from the body with a reduced terminal elimination phase. As used herein, a "controlled-release component" is a compound such as a lipid or mixture of lipids, liposome and/or microsphere that induces the controlled-release of cyclobenzaprine into the subject upon exposure to a certain physiological compound or condition. For example, the controlled-release component can be biodegradable, activated by exposure to a certain pH or temperature, by exposure to an aqueous environment, or by exposure to enzymes. An example of a controlled-release component which is activated by exposure to a certain temperature is a sol-gel. In this embodiment, cyclobenzaprine is incorporated into a sol-gel matrix that is a solid at room temperature. This sol-gel matrix is implanted into a subject having a body temperature high enough to induce gel formation of the sol-gel matrix, thereby releasing the active ingredient into the subject.

Formulation of controlled-release pharmaceutical compositions of the application is within the skill in the art. Controlled release formulations suitable for use in the present application are described in, for example, U.S. Pat. No. 5,674, 533 (liquid dosage forms), U.S. Pat. No. 5,591,767 (liquid reservoir transdermal patch), U.S. Pat. No. 5,120,548 (device comprising swellable polymers), U.S. Pat. No. 5,073,543 (ganglioside-liposome vehicle), U.S. Pat. No. 5,639,476 (stable solid formulation coated with a hydrophobic acrylic polymer), the entire disclosures of which are herein incorporated by reference.

Biodegradable microparticles can also be used to formulate controlled-release pharmaceutical compositions suitable for use in the present application, for example as described in U.S. Pat. Nos. 5,354,566 and 5,733,566, the entire disclosures of which are herein incorporated by reference.

The composition of this application may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The therapeutically effective dose of the composition for the prevention or treatment of agitation, psychosis and/or cognitive decline and associated symptoms thereof in dementia or in a neurodegenerative condition will vary with the type of affliction, the severity of the patient's affliction and the route of administration. The daily dose and dose frequency will also vary according to the age, weight and response of the individual patient. However, the preferred dosage will not equal or exceed 18 mgs per day. In a preferred embodiment, the composition is given in one daily dose at bed time or up to several hours before bedtime to facilitate the achievement of deep, refreshing sleep. Bedtime may be any hour of the day at which a person engages in the most extensive period of sleep.

Any of the methods of treatment described above may be combined with psychotherapeutic behavioral, or environmental intervention to improve the outcome of the treatment. Of particular use is intervention directed at managing agitation including (1) identifying the behavior, (2) understanding the cause of the behavior, and (3) adapting the caregiving environment to remedy the situation. Correctly identifying what has triggered the agitated behavior can often help in selecting the best behavioral intervention. The intervention includes education and support for family and caregivers, structured routines reassurance and socialization, supervision and environmental safety. (See, Alexopoulos et al, 1998).

As used herein, the term "genetic sample" refers to a deoxyribonucleic acid (DNA) sample obtained from a subject. For example, the sample could be collected from tissues or fluids including but not limited to blood, hair, skin, saliva, or cheek swab. A skilled technician could then isolate DNA from the sample using methods well-known in the art and identify the genetic variations of the cytochrome P450 (CYP) genes present in the subject.

In another aspect of this application, a pharmacogenomic test to measure the cytochrome CYP3A4, CYP1A2, CYP3A, and CYP2D6 genotype of a subject suffering from or at risk of developing agitation, psychosis and/or cognitive decline and associated symptoms thereof in dementia or in a neurodegenerative condition, may be used to predict the metabolism of cyclobenzaprine by those subjects and thus this preferred dose to be used. Thus, one aspect of the disclosure of this application provides a method for obtaining a genetic sample from said subject, using said sample to determine the CYP3A, CYP1A2, CYP3A4, or CYP2D6 genotype of said subject, and selecting a therapeutically effective dose of cyclobenzaprine based on that genotype. The CYP3A, CYP1A2, CYP3A4 or CYP2D6 genotype may be determined, for example, by using a gene chip or a PCR technique to identify the alleles of one or more of the genes. Different CYP alleles metabolize cyclobenzaprine at different rates. For individuals having a cytochrome allele known to metabolize cyclobenzaprine more quickly, a higher dose of cyclobenzaprine shall preferably be administered. For individuals having an isoform known to metabolize cyclobenzaprine more slowly, a lower dose of cyclobenzaprine should preferably be administered. The genetic test can be sold as a kit with the product to physicians/lab testing services.

In order that this application to be more fully understood, the following examples are set forth. These examples are for the purpose of illustration only and are not to be construed as limiting the scope of the application in any way. The practice of the application is illustrated by the following non-limiting examples.

EXAMPLES

Example 1

Cyclobenzaprine Sublingual Formulation TNX-102 SL

One sublingual formulation (TNX-102 SL) of the disclosure of this application contains a eutectic complex of cyclobenzaprine hydrochloride (the active ingredient) and D-mannitol. It also contains potassium salt, dibasic. Table 1 shows the composition of the TNX-102 SL tablet.

TABLE 1

TNX-102 SL Sublingual Tablet Composition

| Ingredient | Quality Standard | Function | mg per Tablet | Percent |
|---|---|---|---|---|
| Cyclo-benzaprine hydrochloride | USP | Active ingredient | 2.80$^c$ | 7.37% |
| Mannitol $_a$ | USP, Ph. Eur., JP | Diluent | 2.50 | 6.58% |
| Dye D&C Yellow 10 Lake | FDA approved per 21CFR DMF No. 23720. | Colorant | 0.023 | 0.06% |
| Mannitol/ corn starch (Pearlitol ® Flash) $^b$ | | Diluent | 27.977 | 73.62% |
| Crospovidone | USP, Ph. Eur., JP | Disintegrant | 2.00 | 5.26% |
| Colloidal silica | USP, Ph. Eur., JP | Glidant | 0.50 | 1.32% |

TABLE 1-continued

TNX-102 SL Sublingual Tablet Composition

| Ingredient | Quality Standard | Function | mg per Tablet | Percent |
|---|---|---|---|---|
| Sodium stearyl fumarate | NF, Ph. Eur., JP | Lubricant | 1.00 | 2.63% |
| Potassium phosphate, dibasic | USP, Ph. Eur. | pH control | 1.20 | 3.16% |
| Total | | | 38.00 | 100.00% |

$^a$ Mannitol: about 0.7 mg of the 2.5 mg total amount is a component of the eutectic and the rest is diluent.
$^b$ Pearlitol ® Flash is the trade name for an excipient containing about 80% mannitol and 20% corn starch.
$^c$ Calculated as the HCl salt Example 2

Determining Safety of the TNX-102 SL Formulation in Subjects

To determine the safety of the TNX-102 SL formulation for nighttime administration in human subjects, a total of 10 clinical studies using TNX-102 SL have been completed to date: five Phase 1 studies in healthy volunteers (data not shown), two Phase 2 studies in patients with FM and PTSD; one Phase 3 study in patients with FM; and two open-label extension studies in patients with FM and PTSD. Of the five completed clinical studies in patients with FM and PTSD, a total of 641 patients have received at least one dose of TNX-102 SL administered once daily at bedtime (the "Combined TNX102 SL Safety Population"): 197 PTSD patients and 444 FM patients. Among the PTSD patients, 50 received 5.6 mg (2 sublingual tablets) and the remainder received 2.8 mg (1 sublingual tablet) of TNX-102 SL. See Table 2.

TABLE 2

Patient Exposure in the Completed TNX-102 SL Clinical Studies

| Dose levels | TNX-CY-P201 (AtEase) Placebo-Controlled | TNX-CY-P202 Open-Label Extension (patients | TNX-CY-F202 (BEST-FIT) | TNX-CY-F203 Open-Label Extension | TNX-CY-F301 (AFFIRM) |
|---|---|---|---|---|---|
| Placebo | 94 | — | 101 | — | 256 |
| TNX-102 SL 2.8 mg | 93 | 149$^a$ | 103 | 158$^b$ | 262 |
| TNX-102 SL 5.6 mg | 50 | — | — | — | — |
| Patients per Study | 237 | 149 | 204 | 158 | 518 |
| Patients Exposed to TNX-102 SL (i.e., the Combined TNX-102 SL Safety Population)$^c$ | | | Total | | 641 |
| | | | ≥50 years | | 241 |
| | | | <50 years | | 400 |
| Total Placebo Patients in the Placebo-Controlled Studies (i.e., the Combined Placebo Safety Population) | | | Total | | 451 |
| | | | ≥50 years | | 182 |
| | | | <50 years | | 269 |

$^a$54 patients were in the placebo group and 35 patients were in the 5.6 mg group from the P201 lead-in study.
$^b$79 patients were in the placebo group from the F202 lead-in study.
$^c$Received at least one dose of TNX-102 SL 2.8 mg or 5.6 mg in either a placebo-controlled study or an open-label extension.

Results

Combined TNX-102 SL Safety Population

Overall, TNX-102 SL was well-tolerated in both FM and PTSD patients. The most common adverse events (≥5% incidence) that were considered associated with TNX-102 SL administration were oral hypoaesthesia and oral paraesthesia, and systemic effects such as somnolence and fatigue. All the reported systemic effects were consistent with the side-effect profile of cyclobenzaprine but generally less frequent than those reported in marketed orally ingested formulations such as the immediate release FLEXERIL® and the extended release AMRIX®. No new drug-drug interactions have been identified to date.

Local administration site conditions were not unexpected and are likely a result of the local anesthetic properties of tricyclic molecules due to blockade of sodium channels (Pancrazio et al, 1998). Other than the typically mild and transient local administration site conditions of oral numbness, tingling or burning sensation, bitter taste, and occasional reports of mild to moderate oral irritation that are expected with sublingual TNX-102 SL, the overall adverse event profile at both the 2.8 and 5.6 mg daily doses has been benign.

We also evaluated the safety profile of the blinded safety data (N=71) from the ongoing placebo-controlled, Phase 3 study (TNX-CY-P301) of TNX-102 SL 5.6 mg in patients with military-related PTSD. As of 31 August 2017, the safety profile of those patients is comparable to the adverse event profile observed in the Phase 2 PTSD study (TNX-CY-P201). There were no unexpected systemic adverse events, including no serious central nervous system-related adverse events, and the most common events (≥5% incidence, listed in order of decreasing incidence) were oral hypoesthesia, somnolence and dry mouth.

Incidence of Adverse Events by Age Group

Patients who received at least one dose of TNX-102 SL ranged from 21 to 75 years of age. As summarized in Table 2, of the 641 patients who received at least one dose of TNX-102 SL, 241 were ≥50 and 400 were <50 years of age; the majority received the 2.8 mg dose and only three patients ≥50 years of age received the 5.6 mg dose (age range: 54 to 59 years). No treatment-related, age group-specific safety signals were identified.

Anticholinergic Events

Overall, adverse events identified in the Combined TNX-102 SL Safety Population as associated with TNX-102 SL (occurred in >2 patients and >placebo group in either the Combined TNX102 SL Safety Population, or an age-group subset) that in part may be due to anticholinergic activity are somnolence (5.8%)/sedation (2.2%), fatigue (5.0%), and constipation (2.2%) (note: somnolence and sedation appeared to represent similar adverse events).

The safety data from the AtEase study suggested somnolence and sedation were dose-related, but constipation and fatigue were not. Nearly all of these events in either cohort (TNX-102 SL 2.8 mg or TNX-102 SL 5.6 mg) were mild or moderate in severity. Given that plasma concentrations of cyclobenzaprine after TNX-102 SL administration peak between 4 to 5 hours post-dose, the dosing regimen of TNX-102 SL (once daily at bedtime) possibly minimizes daytime effects of somnolence, sedation, and fatigue.

Among the potentially anticholinergic adverse events that are considered TNX-102 SL related, only constipation and fatigue had a comparatively higher incidence (approximately 2.8-fold and 1.7-fold higher, respectively) in the older population (3.7% and 7.1%, respectively) compared with the younger population; however, this relatively increased incidence in the older age group was also observed in the placebo group.

The following adverse events that may be considered anticholinergic did not occur at an increased incidence in the Combined TNX-102 SL Safety Population compared with the placebo group: dizziness, lethargy, memory impairment, confusional state, disorientation, worsening of balance disorder, dry mouth, dry throat, urinary tract infection, and vertigo. Other potential anticholinergic adverse events, including hallucinations, blurry vision, diplopia, delirium, nasal dryness, dry eye, difficulty urinating, decreased sweating and decreased saliva, were not reported in the Combined TNX-102 SL Safety Population.

Other Adverse Events of Concern

No other adverse events of particular concern, including syncope, dysphagia, contusions, falls, aggression/aggressive behavior (not reported), agitation (not reported), hypotension (not reported), blood pressure decreased (not reported) or any cardiac or hepatic events, appeared to be TNX-102 SL related in either age group.

Dose-Related Adverse Events

The only clinical safety and efficacy study that evaluated two different doses of TNX-102 SL (i.e., 2.8 mg and 5.6 mg) is the AtEase Study/P201 conducted in patients with military-related PTSD (see Table 2). In the AtEase Study, safety data is available for 50 PTSD patients who received at least one dose of TNX-102 SL 5.6 mg. The 5.6 mg dose was well tolerated as demonstrated by a higher completion rate than in the placebo group (83.6% vs 72.8%, respectively), and a lower incidence of study discontinuations due to adverse events than the placebo group (0.0% vs 3.2%, respectively). The safety profile of the 5.6 mg dose was comparable to that of the 2.8 mg dose with the following adverse events demonstrating a possible dose-relationship based on the numerical difference: somnolence/sedation, headache, and possibly glossodynia. Importantly, there was no evidence of an increased risk for suicidal ideation or behaviors associated with TNX-102 SL treatment at either dose.

Example 3

Safety Profile of Oral Cyclobenzaprine Marketed Products

To evaluate the safety profile of oral cyclobenzaprine marketed products and potential concern with drug interaction with marketed Alzheimer's disease medications, an extensive search was conducted using public database and literatures, including PubMed, NIH Drug Reaction Navigator, Medscape Drug Interaction Checker, Drugs.com and U.S. Food and Drug Administration (FDA) Adverse Event Reporting System (FAERS). Two types of oral cyclobenzaprine formulations are available in the market—cyclobenzaprine IR (5 mg or 10 mg TID; i.e., FLEXERIL) and cyclobenzaprine ER (15 mg BID or QD or 30 mg QD; i.e., AMRIX). Both formulations are administered at doses that are typically at least 2- to 3-fold higher than TNX-102 SL 5.6 mg administered sublingually once-a-day at bedtime, proposed for the treatment of agitation in dementia.

Of note, these safety data are based on administration of doses higher than the cyclobenzaprine 5.6 mg daily dose preferred in this application, and thus would be expected to be associated with increased side effects. The adverse events most commonly reported with both formulations (FLEXERIL and AMRIX) include drowsiness/somnolence, dry mouth, dizziness, and fatigue, as well as constipation, nausea, and dyspepsia, which were frequently reported in patients who particularly received the cyclobenzaprine ER formulation (AMRIX Package Insert, 2016; FLEXERIL Package Insert, 2013). There was a low incidence of adverse events of particular concern in the elderly and/or events considered anticholinergic in patients who received FLEXERIL 10 mg reported in clinical studies or in the post-market. Confusion and blurred vision were reported in 1% to 3% of patients. The following were reported in <1% of patients: cardiovascular events (tachycardia, arrhythmia, vasodilation, palpitation, and hypotension), nervous system and psychiatric adverse events (such as seizures, agitation, vertigo, disorientation, agitation, hallucinations, and diplopia) and urinary retention (AMRIX Package Insert, 2016; FLEXERIL Package Insert, 2013). Notably, in a post-marketing surveillance performed in 1980 (N=6,311) after two decades of experience and more than 100,000,000 prescriptions of cyclobenzaprine 10 mg, the incidence of hallucinations was found to be 0.2%, mostly in elderly patients, with events mostly reversible and likely dose-related, as none were reported among patients who took 5 mg TID (FLEXERIL® OTC Switch NDA 21079 FDA Safety Review: Jul. 20, 1999).

These findings indicate that the preferred TNX-102 SL formulation will have minimal side effects in the elderly population with agitation, psychosis and/or cognitive decline and associated symptoms thereof in dementia or in a neurodegenerative condition.

Example 4

Studies of Cyclobenzaprine in the Elderly

The effects of cyclobenzaprine IR 5 mg upon psychomotor function were investigated in healthy elderly volunteers (62 to 80 years of age, N=17) in a crossover study of cyclobenzaprine IR 5 mg TID, diphenhydramine 50 mg TID, and placebo (Lines et al., 1997). Each treatment was administered as 10 doses over 4 days. In this patient population, there was no evidence of drowsiness or impaired cognitive test performance. Of note, less sedative and cognitive impairment was observed in this elderly population than compared with a younger population in a prior study. Consistent with this finding, results from a psychomotor function study performed by the manufacturer (Merck; FLEXERIL® OTC Switch NDA 21079 FDA Safety Review: Jul. 20, 1999) also demonstrated that there was no consistent pattern of impairment of psychomotor function as measured by computerized test batteries, including assessments of driving-related skills in elderly patients (≥65 years of age, N=32), with the performance being similar to the younger population (21 to 49 years of age).

Precautions Regarding Use of Anticholinergics and Muscle Relaxants in the Elderly There are recommendations of potentially inappropriate medication use in older adults (e.g., the Beers Criteria;

American Geriatric Society, 2015). Drugs with anticholinergic activity that are muscle relaxants are listed as potentially inappropriate, primarily due to effects on cognitive function and adverse events secondary to nervous system effects, such as falls. Cyclobenzaprine (IR 5 to 10 mg TID and ER 15 mg BID/QD to 30 mg QD) was given a score of 2 on a scale of to 3 in an anticholinergic burden scale (Rudolph et al., 2008), primarily due to its anticholinergic activity, as well as its long half-life. It should be noted that these recommendations are based on higher doses than the TNX-102 SL dose proposed in this application studying a target population with caregivers. The most commonly reported anticholinergic adverse event associated with the administration of cyclobenzaprine is dose-related dry mouth; this is considered tolerable and of minimal clinical importance considering the potential clinical benefit of TNX-102 SL. Other potential anticholinergic effects in patients who received cyclobenzaprine IR 10 mg were all reported at a low incidence: tachycardia (<1%), urinary retention (<1%), confusion (1% to 3%) and blurred vision (1% to 3%). Data are not available for cyclobenzaprine 5 mg IR. Overall, adverse central nervous system effects and poorer cognitive and functional outcomes in drugs associated with high anticholinergic burden scores have generally not been observed with cyclobenzaprine (i.e., incidence of <1% to 3%).

Drug-Drug Interactions

For the treatment of agitation, psychosis and/or cognitive decline and associated symptoms thereof in dementia or in a neurodegenerative condition, most patients will likely be taking one of the four currently prescribed drugs for dementia (donepezil, rivastigmine, galantamine, and memantine). Three of these drugs (donepezil, rivastigmine, and galantamine) have anticholinesterase activity as the mechanism of action. As such, their product labeling recommends avoiding the co-administration of anticholinergics due to opposing activities. Cyclobenzaprine is not specifically mentioned and a search of drug-drug interactions between cyclobenzaprine and these four drugs in PubMed, NIH Drug Reaction Navigator, Medscape Drug Interaction Checker, and Drugs.com did not identify any reports of interactions.

In addition, a preliminary search of the FDA Adverse Event Reporting System (FAERS) was conducted to identify all reported AEs during the first quarter of 2017 for which AD drugs and cyclobenzaprine were both reported to be suspected drugs. The following product active ingredient were used to retrieve AD drug-related events from the FAERS database as either the primary or secondary suspect drug: "DONEPEZIL", "RIVASTIGMINE", "GALANTAMINE", "MEMANTINE". These events were then filtered to select events with "CYCLOBENZAPRINE" as any source of suspicion. Of the 296 unique cases retrieved using the above search criteria and filters, only one case was identified for which both cyclobenzaprine and an AD drug (galantamine) were listed as suspect drugs. As the patient was on numerous medications, neither drugs were the primary suspect. Additional details from this case is presented as follows. A 77-years old female patient (case ID: 13227232) who was on multiple medications was identified. The reported adverse events included balance disorder, cognitive disorder, constipation, fall, hypotension, multiple drug therapy, orthostatic hypotension, sedation and toxicity to various agents. The patient had morphine sulfate as primary suspect for the reported adverse events, and cyclobenzaprine and galantamine in addition to another 23 drugs as secondary suspects.

Guidance for Cyclobenzaprine Use in the Elderly

Pharmacokinetics data have demonstrated that the plasma concentration of cyclobenzaprine is increased in the elderly compared to younger subjects (up to 1.7-fold or 1.4-fold higher for the IR and ER formulations, respectively. Thus, for cyclobenzaprine IR, it is recommended to initiate treatment with a 5 mg dose with the option to titrate slowly upward. It is also noted in the product labeling for cyclobenzaprine IR, "given that the elderly may be more at risk for central nervous adverse events such as hallucinations and confusion, cardiac events resulting in falls or other sequelae, drug-drug and drug-disease interactions, it is recommended that it only be used if clearly needed" (FLEXERIL Package Insert, 2013). However, the administration of extended release cyclobenzaprine (AMRIX 30 mg or 15 mg capsules) is not recommended in the elderly since its dosing flexibility is more limited due to its once-a-day dosing regimen (AMRIX Package Insert, 2016).

Conclusions

To date, the safety profile of TNX-102 SL and the other marketed cyclobenzaprine products, particularly at the lower dose typical for the elderly (e.g., cyclobenzaprine 5 mg IR TID which is more than 2-fold higher than the preferred dose of TNX-102 SL for agitation in dementia), is favorable and well tolerated with a very low incidence of systemic anticholinergic effects. As summarized above, the safety profile of cyclobenzaprine at daily doses up to 30 mg is mostly mild to moderate and well tolerated. In addition, the unique formulation of TNX-102 SL enabling rapid transmucosal absorption, bypass of first-pass hepatic metabolism, and reduced production of a long half-life active metabolite, norcyclobenzaprine, minimizes daytime effects when dosed once daily at bedtime.

The most commonly reported adverse events with marketed cyclobenzaprine products include drowsiness/somnolence, dry mouth, dizziness, and fatigue whereas the most commonly reported drug-related events with TNX-102 SL are local administration site conditions such as oral hypoaesthesia and paraesthesia, and systemic effects of somnolence/sedation and headache. Dizziness, which could be of particular concern for the elderly, has not been reported at an increased incidence in the TNX-102 SL treated groups compared with placebo groups.

Analysis of anticholinergic events incidence and other events of particular concern for the elderly by age group among TNX-102 SL-treated patients demonstrated that only constipation and fatigue were considered TNX-102 SL-related, and had comparatively higher incidences in patients ≥50 years of age compared to patients <50 years of age, albeit at relatively low rates (approximately 2.8-fold and 1.7-fold higher, respectively).

Of relevance for the treatment of agitation in dementia, no drug-drug interactions with cyclobenzaprine and the currently approved dementia drugs were identified, thereby allowing the patients to continue with their standard of care.

The preferred dose of TNX-102 SL for the treatment of agitation, psychosis and/or cognitive decline and associated symptoms thereof in dementia or in a neurodegenerative condition is about 5.6 mg (2×about 2.8 mg tablets), which is more than 2-fold lower than the lowest recommended cyclobenzaprine dosing regimens (e.g., cyclobenzaprine IR 5 to 10 mg TID or cyclobenzaprine ER 15 BID/QD to 30 mg QD). The safety data from the marketed cyclobenzaprine drug products and the TNX-102 SL clinical studies described herein support a favorable safety profile of once daily dosing of TNX-102 SL 5.6 mg to be used at bedtime in the dementia and/or a neurodegenerative condition patient population over the age of 50 years.

Example 5

Efficacy, Safety and Tolerability of TNX-102 SL for the Treatment of Agitation, Psychosis and/or Cognitive Decline and Associated Symptoms thereof in Dementia or in a Neurodegenerative Condition A randomized double-blind placebo-controlled fixed dose study of TNX-102-SL for the treatment of agitation in Alzheimer's Disease (AAD) is conducted over 8 weeks. The effects of TNX-102-SL 5.6 mg (2×2.8 mg tablets) are studied in subjects ranging from 50 to 90 years of age diagnosed with probable Alzheimer's Disease, who experience clinically significant, moderate or severe agitation as defined by the International Psychogeriatric Association Agitation Definition Work Group (Cummings et al, 2015). The subjects have a Clinical Global Impression of Severity (CGIS) score greater than or equal to 4 (moderately ill) at Screening and Baseline. The subjects may be using medication for the treatment of Alzheimer's Disease (e.g., donepezil, rivastigmine, galantamine, memantine) provided the dose is stable for at least 3 months prior to randomization in the study. TNX-102-SL (2×2.8 mg tablets taken sublingually each day at bedtime) is compared to placebo during an 8-week evaluation period.

Efficacy Endpoints

The Primary Efficacy Endpoint is the mean change from Baseline in the Cohen Mansfield Agitation Inventory (CMAI) after 8 weeks of treatment (measured at baseline and at each visit). The key Secondary Efficacy Endpoints include (1) Modified Alzheimer's Disease Cooperative Study Clinical Global Impression of Change Agitation Domain Score (mADCS-CGIC-Agitation) after 8 weeks of treatment, (2) Mean change from baseline in the CMAI total score after 4 weeks of treatment, (3) Mean change from baseline in the CMAI total score after 2 weeks of treatment, (4) Mean change from baseline in the CMAI Physical/Aggressive subscale score after 8 weeks of treatment, (5) Mean change from baseline in the CMAI Physical/Non-Aggressive subscale score after 8 weeks of treatment, (6) Mean change from baseline in the CMAI Verbal/Aggressive subscale score after 8 weeks of treatment, (7) Mean change from baseline in the Alzheimer's Disease Assessment Scale-Cognition (ADAS-Cog) score after 8 weeks of treatment. A sequential test procedure may be applied to the above secondary endpoints to adjust for multiplicity and to control for overall type I error.

Exploratory Efficacy Endpoints include (1) Change from baseline in the Neuropsychiatric Inventory (NPI) Agitation/Aggression Domain Score after 8 weeks of treatment, (2) Change from baseline in the NPI Irritability/Lability Domain Score after 8 weeks of treatment, (3) Change from baseline in the NPI Caregiver Distress Score after 8 weeks of treatment, (4) CGIS Agitation Domain Score after 8 weeks of treatment, (5) Zarit Burden Interview (ZBI), (6) ADCS-CGIC-Overall score after 8 weeks of treatment, (7) CGIS-Agitation, change from baseline to Week 8, (8) Proportion of patients using rescue medication (recorded in the Medication Administration Record or caregiver diary), (9) Patient Global Impression of Change (PGIC-rated by caregiver) score after 8 weeks of treatment, (10), Change from baseline in the Sleep Disorders Inventory (SDI) score after 8 weeks of treatment, (11) Change from baseline activity level and change from baseline sleep parameters as monitored by the ActiGraph device after 8 weeks of treatment, and (12) Change from baseline in activities of daily living as assessed by the Alzheimer's Disease Cooperative Study Activities of Daily Living Inventory 19 items (ADCS-$ADL_{19}$).

Safety

Safety is assessed by Adverse events (AE) and serious AEs (SAEs) throughout the entire duration of the study, may include detailed assessment of AEs involving the oral cavity, changes from baseline in clinical laboratory test results, changes from baseline in vital signs including but not limited to body temperature and weight, changes from baseline in electrocardiogram (ECG) parameters, changes from baseline in the Columbia-Suicide Severity Rating Scale (C-SSRS) score), changes from baseline in the Mini Mental State Examination (MMSE) score, changes from baseline in the ADAS-Cog score, changes from baseline in the Delirium Rating Scale-Revised-98 (DRS-R-98) score (Trzepacz 2001), and Protocol-defined anticholinergic adverse events of special interest including orthostatic blood pressure changes of >20 mmHg (systolic) or >10 mmHg (diastolic), acute cognitive changes consistent with a DSM-5 diagnosis of delirium, clinically relevant cognitive deterioration, confusion, falls, hallucinations, hypohidrosis, and fever.

Pharmacokinetic Endpoint

Blood levels of cyclobenzaprine and norcyclobenzaprine after 3 and 8 weeks of daily treatment are determined.

Pharmacogenomic Endpoints

Potential genetic determinants of treatment response are examined by studying functional variants of several genes in relation to treatment outcome. Agitation and other neurobehavioral disturbances in Alzheimer's disease have long been known to have associations with dysregulation of monoaminergic neurotransmission. Genetic variants of several genes involved in monoaminergic pathways have been associated with agitation in dementia including serotonin and dopamine (Pritchard et al., 2007; Proitsi et al., 2012). Genetic variants of the 5-HT2A receptor and the 5-HT2C receptor have been associated with therapeutic responses to citalopram treatment of agitation in Alzheimer's disease (Peters, et al., 2016). In the present study, we examine potential genetic determinants of treatment response by studying functional variants of several genes in relation to treatment outcome. The genetic variants include but are not limited to: the 5-HT2A serotonin receptor (HTR2A-T102C), the 5-HT2C serotonin receptor (HTR2C-Cys23Ser), the serotonin transporter (5HTT-LPR), brain-derived neurotropic factor (BDNF-Val66-Met), and apolipoprotein E ($\epsilon2$, $\epsilon3$, $\epsilon4$ variants).

A single blood sample is obtained at Baseline (Visit 2) from patients who have signed a separate informed consent form for analysis of potential genetic variants and relevant biomarkers.

Statistical Methods

All subjects who receive at least 1 dose of study drug are analyzed in the safety assessment. All randomized subjects for when at least a baseline and one post-baseline CMAI are assessed are analyzed in the Modified Intent-to-Treat Population (mITT) assessment. All randomized subjects who receive at least one dose of TBX-102 SL and from whom an evaluable pharmacokinetic (PK) blood sample is obtained are analyzed in the PK assessment.

Efficacy Analysis (mITT Population)—Endpoints

The primary efficacy endpoint is the change from Baseline to Week 8 in the composite CMAI scores. The primary efficacy analysis is performed using a mixed model repeated measures (MMRM) approach, with comparisons being made between the patients treated with TNX-102 SL and patients treated with concurrent placebo. The model includes all patients in the mITT population, and the dependent variable is the observed change from baseline in the total CMAI score at each post-randomization visit. Covariates in the model include the fixed categorical effects of treatment, site, location type (nursing home or community), visit, and treatment-by-visit interaction, as well as the continuous fixed covariates of baseline CMAI score and baseline score-by-visit interaction.

Continuous secondary efficacy endpoints analyses are performed using the MMRM methodology, and the analyses are based on the mITT population. Significance tests of treatment differences are tested at the two-sided 0.05 level and the corresponding 95% confidence intervals are calculated. To adjust for multiplicity and to control for overall type I error, a sequential test procedure is applied to the secondary efficacy endpoints.

Safety Analyses (Safety Population)

Adverse events are coded using the latest version of the Medical Dictionary for Regulatory Activities (MedDRA) and are summarized overall and by preferred term and system organ class. Adverse events are also summarized by severity and relationship to study drug. Serious AEs and AEs leading to discontinuation of study drug are also summarized. Actual values and changes from Baseline for clinical laboratory test results, vital sign measurements, ADAS-Cog, DRS-R-98, and MMSE scores are summarized at endpoint using descriptive statistics (n, mean, SD, median, minimum, and maximum). Examination of the oral cavity is conducted to assess the safety of sublingual administration and pregnancy tests are conducted for females of childbearing potential.

Sample Size Estimation

Approximately 160 subjects total in a 1:1 randomization, that is 80:80 subjects for TNX-102 SL 5.6 mg and placebo groups are enrolled in the study. Determination of effect size for design of definitive confirmatory studies are enabled by a sample size of 80 patients per arm.

Blood Sample Collection

Blood samples are collected at Baseline, and weeks 3 and 8 for population pharmacokinetic and pharmacogenomics analyses.

Expected Results

TNX-102 SL 5.6 mg (2×2.8 mg tablets) is safe, well-tolerated, and efficacious for the treatment of AAD over the 8-week study period.

Example 6

Long-Term Safety and Tolerability of TNX-102 SL for the Treatment of AAD

The long-term safety and tolerability of TNX-102 SL is assessed in an open-label, multicenter, fixed-dose study for up to 44 weeks for the treatment of agitation in subjects with Alzheimer's disease (n=160; 50-90 years; males and females with AAD). Subjects who have safely completed the double-blind study (see Example 5) without significant adverse events that are related to study drug are eligible for the open-label extension study. Subjects who continue to meet criteria for probable Alzheimer's disease and have a reliable caregiver willing to comply with study procedures are retained in the study. Patients who have developed significant medical conditions that, in the opinion of the investigator or medical monitor, may interfere with safety assessments are excluded from the study. At the baseline visit, all subjects receive open-label TNX-102 SL 5.6 mg at bedtime.

The primary efficacy endpoints to measure the assessment of long-term efficacy of TNX-102 SL is mean change from Baseline in the CMAI. Among key Secondary Efficacy Endpoints are assessment of the NPI Agitation/Aggression domain, and mADCS-CGIC-Agitation. Safety and tolerability of TNX-102 SL is assessed by reported adverse events (AEs), physical and neurological examinations, vital signs (including orthostatic blood pressure), clinical laboratory assessments, resting 12-lead ECGs, S-STS, and MMSE. Daytime somnolence is assessed by the MTRSS. A focused examination of the oral cavity is conducted periodically to assess safety of sublingual administration of study drug. Pregnancy tests are conducted for females of childbearing potential.

Exploratory Efficacy Endpoints evaluated include (1) Change from baseline in the Neuropsychiatric Inventory (NPI) Agitation/Aggression Domain Score, (2) Change from baseline in the NPI Irritability/Lability Domain Score, (3) Change from baseline in the NPI Caregiver Distress Score, (4) CGIS Agitation Domain Score, (5) Zarit Burden Interview (ZBI), (6) ADCS-CGIC-Overall score, (7) CGIS-Agitation, change from baseline to Week 44, (8) Proportion of patients using rescue medication (recorded in the Medication Administration Record or caregiver diary), (9) Patient Global Impression of Change (PGIC-rated by caregiver) score after 44 weeks of treatment, (10), Change from baseline in the Sleep Disorders Inventory (SDI) score after 44 weeks of treatment, (11) Change from baseline activity level and change from baseline sleep parameters as monitored by the ActiGraph device after 44 weeks of treatment, and (12) Change from baseline in activities of daily living as assessed by the Alzheimer's Disease Cooperative Study Activities of Daily Living Inventory 19 items (ADCS-ADL$_{19}$).

Expected Results

TNX-102 SL 5.6 mg (2×2.8 mg tablets) is safe, well-tolerated, and efficacious for the treatment of AAD over the 44-week study period.

All references cited herein are incorporated by reference. The present application may be embodied in other specific forms without departing from the spirit or essential attributes thereof and, accordingly, reference should be made to the appended claims, rather than to the foregoing specification, as indication the scope of the application.

REFERENCES

1. Alexopoulos G. S. et al. (1998) The Expert Consensus Series Guidelines. Treatment of Agitation in Older Persons with Dementia. Postgraduate Medicine Special Report (March).
2. Alzheimer's Association (2004) Agitation and Alzheimer's Disease Fact Sheet.
3. Assal F. et al. (2004) Association of the serotonin transporter and receptor gene polymorphisms in neuropsychiatric symptoms in Alzheimer disease. Arch Neurol. August; 61(8):1249-53.
4. Balant L. P. et al. (1990) Prodrugs for the Improvement of Drug Absorption Via Different Routes of Administration, Eur. J. Drug Metab. Pharmacokinet. 15:143-153.
5. Bund-gaard, H. (1991) Novel Chemical Approaches in Prodrug Design, Drugs of the Future 16:443-458.
6. Canevelli, M et al. (2016). Sundowning in Dementia: Clinical Relevance, Pathophysiological Determinants, and Therapeutic Approaches. Frontiers in medicine, 3.
7. Chaves, R. S. et al (2010). Protein aggregation containing beta-amyloid, alpha-synuclein and hyperphosphorylated tau in cultured cells of hippocampus, substantia nigra and locus coeruleus after rotenone exposure. BMC Neuroscience 11:144.
8. Cummings J, et al. (2014). Agitation in cognitive disorders: International Psychogeriatric Association provisional consensus clinical and research definition. Int Psychogeriatr. 2014 October 14:1-11.
9. Cummings J et al. (2017) Alzheimer's disease drug development pipeline: 2017. Alzheimers Dement (N Y). 2017 May 24; 3(3):367-384.
10. Diaz-Olavarrieta C. et al. (1999) Neuropsychiatric manifestations of multiple sclerosis. J Neuropsychiatry Clin Neurosci.; 11(1):51-7.
11. Drye L. T. et al. (2012) Citalopram for agitation in Alzheimer's disease: Design and methods. *Alzheimers Dement.;* 8(2):121-130.
12. Esiri M. M. (1996) The basis for behavioural disturbances in dementia. J Neurol Neurosurg Psychiatry. August; 61(2):127-30.
13. Fleisher, A. S. et al. (2007). Clinical predictors of progression to Alzheimer disease in amnestic mild cognitive impairment. Neurology, 68(19), 1588-1595.
14. Folstein, M. F. et al. (1975). "Mini-mental state": a practical method for grading the cognitive state of patients for the clinician. Journal of psychiatric research, 12(3), 189-198.
15. Gareri P. (2014) Use and Safety of Antipsychotics in Behavioral Disorders in Elderly People With Dementia J Clin Psychopharmacol; 34: 109-123.
16. Greenblatt H. K. and Greenblatt D. J. (2016) Use of Antipsychotics for the Treatment of Behavioral Symptoms of Dementia. J Clin Pharmacol. September; 56(9): 1048-57.
17. Kar N. (2009) Behavioral and psychological symptoms of dementia and their management. Indian J Psychiatry. January; 51 Suppl 1:S77-86.
18. Katz W A and Dube J. (1988) Cyclobenzaprine in the treatment of acute muscle spasm: review of a decade of clinical experience. Clin Ther.; 10(2):216-28.
19. Kerner N. A. and Roose S. P. (2016) Obstructive Sleep Apnea is Linked to Depression and Cognitive Impairment: Evidence and Potential Mechanisms. Am J Geriatr Psychiatry. 2016 June; 24(6):496-508.
20. Macedo A. C., et al. (2017) Is Sleep Disruption a Risk Factor for Alzheimer's Disease? J Alzheimers Dis. 58(4):993-1002.
21. Mansfield, J. C. (1991) Instruction Manual for the Cohen Mansfield Agitation Inventory.
22. McCurry S. M. et al. (2011) Increasing walking and bright light exposure to improve sleep in community-dwelling persons with Alzheimer's disease: results of a randomized, controlled trial. J Am Geriatr Soc. August; 59(8):1393-402.
23. Moldofsky H. et al. (2011) Effects of bedtime very low dose cyclobenzaprine on symptoms and sleep physiology in patients with fibromyalgia syndrome: a double-blind randomized placebo-controlled study. J Rheumatol. December; 38(12):2653-63.
24. Moldofsky H. et al. (2015) Relationship of Sleep Quality and Fibromyalgia Outcomes in a Phase 2b Randomized, Double-Blind, Placebo-Controlled Study of Bedtime, Rapidly Absorbed, Sublingual Cyclobenzaprine (TNX-102 SL). Arthritis Rheumatol.; 67 (suppl 10).
25. Peters, M. E., et al. (2016) Citalopram for the treatment of agitation in Alzheimer dementia: genetic influences. Journal of geriatric psychiatry and neurology; 29(2):59-64.
26. Pritchard, A. L. et al. (2007) Role of serotonin transporter polymorphisms in the behavioural and psychological symptoms in probable Alzheimer disease patients. Dementia and geriatric cognitive disorders; 24(3):201-206.
27. Proitsi, P. et al. (2012) Association of serotonin and dopamine gene pathways with behavioral subphenotypes in dementia. Neurobiology of aging; 33(4):791-803.
28. Rosa M. A. and Lisanby S. H. (2012) Somatic treatments for mood disorders. Neuropsychopharmacology. January; 37(1):102-16.
29. Rose K, et al. (2015) Correlates among nocturnal agitation, sleep, and urinary incontinence in dementia. Am J Alzheimers Dis Other Demen. February; 30(1): 78-84.
30. Ross C. A. and Poirier M. A. (2004). Protein aggregation and neurodegenerative disease. Nat Med. 2004 July; 10 Suppl:S10-7.
31. Sachdev P S, et al. (2015) DSM-5 and Mental Disorders in Older Individuals: An Overview. Harv Rev Psychiatry. 2015 September-October; 23(5):320-8.
32. Schneider L. S. et al. (2005) Risk of death with atypical antipsychotic drug treatment for dementia: meta-analysis of randomized placebo-controlled trials. JAMA. October 19; 294(15):1934-43.
33. Schneider L. S. et al., (2006) Efficacy and adverse effects of atypical antipsychotics for dementia: metaanalysis of randomized, placebo-controlled trials. Am J Geriatr Psychiatry. March; 14(3):191-210.

34. Shih, Y. H. et al. (2017). Sundown Syndrome, Sleep Quality, and Walking Among Community-Dwelling People With Alzheimer Disease. Journal of the American Medical Directors Association, 18(5), 396-401.

35. Sura L, et al. (2012) Dysphagia in the elderly: management and nutritional considerations. Clin Interv Aging. 7:287-98.

36. Trzepacz P T, et al. (2001) Validation of the Delirium Rating Scale-revised-98: comparison with the delirium rating scale and the cognitive test for delirium. J Neuropsychiatry Clin Neurosci. 2001 Spring; 13(2): 229-242. Erratum in: J Neuropsychiatry Clin Neurosci. 2001 Summer; 13(3):433.

37. Wang L. Y. (2009) Prazosin for the treatment of behavioral symptoms in patients with Alzheimer disease with agitation and aggression. Am J Geriatr Psychiatry. September; 17(9):744-51.

38. Weaver et al. (1997) An instrument to measure functional status outcomes for disorders of excessive sleepiness. Sleep. 20(10):835-43.

39. Weintraub D and Katz I. R. Pharmacologic interventions for psychosis and agitation in neurodegenerative diseases: evidence about efficacy and safety. Psychiatr Clin North Am. 2005 December; 28(4):941-83.

40. Williamson D. R. et al. (2016). Pharmacological interventions for agitation in patients with traumatic brain injury: protocol for a systematic review and meta-analysis. Syst Rev. November 17; 5(1):193.

41. World Health Organization Dementia Fact Sheet (2017).

42. Xie L. et al. (2013) Sleep drives metabolite clearance from the adult brain. Science. 2013 Oct. 18; 342(6156): 373-7.

43. U.S. Patent Application No. US20110124656A1. Methods and Compositions for Treating Symptoms Associated with Post-Traumatic Stress Disorder using Cyclobenzaprine.

44. U.S. Pat. No. 6,395,788. Methods and compositions for treating or preventing sleep disturbances and associated illnesses using very low doses of cyclobenzaprine.

45. U.S. Pat. No. 6,358,944. Methods and compositions for treating generalized anxiety disorder.

46. International Patent Application No. WO2013188847 Compositions and Methods for Transmucosal Absorption.

47. Trzepacz P T, et al. J Neuropsychiatry Clin Neurosci. 2001 Spring; 13(2):229-242. Erratum in: J Neuropsychiatry Clin Neurosci. 2001 Summer; 13(3):433.

The invention claimed is:

1. A method for treating or preventing one or more agitation associated symptoms of dementia, the agitation associated symptoms being selected from the group consisting of rapid changes in mood, rapid changes in irritability, rapid changes in outbursts, delusions, hallucinations, checking and rechecking doors or appliances, tearing tissues, uncharacteristic cursing or threatening language, delirium, aggression, verbal aggression, physical aggression, combativeness, lability of mood, anger, akathisia, compulsions, obsessivity, impairment of interpersonal relationships, impairment of social functioning, impairment to perform or participate in daily living activities, and urinary incontinence, the method comprising administering to a subject in need or at risk thereof, a pharmaceutical composition comprising a eutectic of cyclobenzaprine HCl and mannitol and a pharmaceutically acceptable carrier, the composition providing 5.6 mg or less per day of the cyclobenzaprine HCl to said subject.

2. The method of claim 1, wherein the pharmaceutical composition is administered daily.

3. The method of claim 2, wherein the composition comprises cyclobenzaprine HCl in an amount of
    (a) less than 5 mg;
    (b) 5.6 mg; or
    (c) 2.8 mg.

4. The method of claim 3, wherein the composition is administered simultaneously as two dosage units, wherein each dosage unit comprises 2.8 mg of cyclobenzaprine HCl or wherein the combined amount in the two dosage units is 5.6 mg of cyclobenzaprine HCl.

5. The method of any one of claims 1, 4, 2 and 4, wherein the composition is administered once daily.

6. The method of claim 1, wherein the pharmaceutical composition is in a dosage form selected from a tablet, a scored tablet, a coated tablet, an orally dissolving tablet, a suppository, a thin film, a powder, a caplet, a capsule, a troche, a dragee, a dispersion, a suspension, a solution, or a patch.

7. The method of claim 1, wherein the pharmaceutical composition is administered sublingually, buccally, orally, intravenously, intramuscularly, subcutaneously, inhalationally, intranasally, transdermally, parenterally, rectally, or vaginally.

* * * * *

UNITED STATES PATENT AND TRADEMARK OFFICE
CERTIFICATE OF CORRECTION

| | | |
|---|---|---|
| PATENT NO. | : 11,826,321 B2 | Page 1 of 1 |
| APPLICATION NO. | : 16/215952 | |
| DATED | : November 28, 2023 | |
| INVENTOR(S) | : Herbert W. Harris and Seth Lederman | |

It is certified that error appears in the above-identified patent and that said Letters Patent is hereby corrected as shown below:

In the Claims

Claim 5, Column 26, Line 35, please delete "claims 1, 4, 2 and 4," and replace with --claims 1, 2, 3 and 4,--.

Signed and Sealed this
Ninth Day of January, 2024

*Katherine Kelly Vidal*

Katherine Kelly Vidal
*Director of the United States Patent and Trademark Office*